(12) United States Patent
Parkar et al.

(10) Patent No.: US 11,553,996 B2
(45) Date of Patent: Jan. 17, 2023

(54) RADIATION CURABLE COMPOSITIONS AND COMPOSITE ARTICLES MADE USING AN ADDITIVE MANUFACTURING PROCESS

(71) Applicant: 3M INNOVATIVE PROPERTIES COMPANY, St. Paul, MN (US)

(72) Inventors: Zeba Parkar, Marietta, GA (US); James D. Hansen, White Bear Lake, MN (US); Tianyu Wu, St. Paul, MN (US); Carsten Franke, St. Paul, MN (US); Timothy D. Dunbar, Woodbury, MN (US); Gregory A. Kobussen, Woodbury, MN (US); Ahmed S. Abuelyaman, Woodbury, MN (US); Bradley D. Craig, Lake Elmo, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 273 days.

(21) Appl. No.: 16/640,089

(22) PCT Filed: Aug. 22, 2018

(86) PCT No.: PCT/IB2018/056371
§ 371 (c)(1),
(2) Date: Feb. 19, 2020

(87) PCT Pub. No.: WO2019/048963
PCT Pub. Date: Mar. 14, 2019

(65) Prior Publication Data
US 2020/0197138 A1   Jun. 25, 2020

Related U.S. Application Data

(60) Provisional application No. 62/556,649, filed on Sep. 11, 2017.

(51) Int. Cl.
| | |
|---|---|
| *C08K 7/16* | (2006.01) |
| *C08F 2/46* | (2006.01) |
| *C08F 2/50* | (2006.01) |
| *C08G 61/04* | (2006.01) |
| *A61C 13/00* | (2006.01) |
| *B33Y 10/00* | (2015.01) |
| *B33Y 30/00* | (2015.01) |

(Continued)

(52) U.S. Cl.
CPC ...... *A61C 13/0013* (2013.01); *A61C 13/0004* (2013.01); *A61K 6/17* (2020.01); *A61K 6/887* (2020.01); *B29C 64/124* (2017.08); *B33Y 10/00* (2014.12); *B33Y 30/00* (2014.12); *B33Y 70/10* (2020.01); *C08F 222/102* (2020.02); *C08F 222/1025* (2020.02); *C08F 222/1067* (2020.02); *C08K 3/36* (2013.01); *C08K 9/02* (2013.01); *B29K 2509/02* (2013.01); *B29L 2031/7536* (2013.01); *B33Y 80/00* (2014.12); *C08F 222/1065* (2020.02)

(58) Field of Classification Search
CPC .......... C08F 222/1067; C08F 222/1025; C08F 222/102; C08F 222/10; C08F 222/1065; C08F 22/10; C08F 2/48; A61K 6/65; A61K 6/62; A61K 6/17; A61K 6/887; C08K 9/02; C08K 3/36; C08K 2509/02; B29L 2031/7536; A61C 13/0013; A61C 13/087; A61C 13/082; A61C 13/0004; B33Y 10/00; B33Y 70/00; B33Y 30/00; B33Y 80/00; B29C 64/124; C08L 33/08
USPC .............. 523/223, 1; 522/6, 189, 184, 71, 1; 520/1

See application file for complete search history.

(56) References Cited

U.S. PATENT DOCUMENTS

| | | | |
|---|---|---|---|
| 3,429,722 | A | 2/1969 | Economy |
| 3,479,310 | A | 11/1969 | Dieterich |

(Continued)

FOREIGN PATENT DOCUMENTS

| | | | |
|---|---|---|---|
| CN | 86102967 | A | 12/1986 |
| CN | 1865295 | A | 11/2006 |

(Continued)

OTHER PUBLICATIONS

Wolter et al., WO2017036885 Machine Translation, Mar. 9, 2017 (Year: 2017).*
Martini, Optical Brighteners, 2000, Polymer Modifiers and Additives, pp. 393-418 (Year: 2000).*
Dehurtevent, "Stereolithography: A New Method for Processing Dental Ceramics by Additive Computer-Aided Manufacturing," Dental Materials, Mar. 2017, vol. 33, No. 5, pp. 477-485.

(Continued)

*Primary Examiner* — Jessica Whiteley
(74) *Attorney, Agent, or Firm* — Adrian L. Pishko

(57) ABSTRACT

A radiation curable composition including at least one radiation hardenable component, a photo-initiator, and a filler material having a population of particulates in an amount greater than or equal to 50% by weight of the printable composition. The population of particulates exhibits a median diameter (D50) of greater than or equal to 0.3 micrometer on a volume-average basis as determined using the Particle Size Test Method, and the radiation curable composition exhibits a viscosity of less than or equal to 150 Pa s when measured using the Viscosity Test Method. A method, apparatus, and systems for producing composite articles by selectively exposing a portion of the radiation curable composition to a source of actinic radiation to at least partially cure the exposed portion of the radiation curable composition, thereby forming a hardened layer, preferably by an additive manufacturing process such as stereophotolithography, are also described. The composite articles may include composite dental restorations.

16 Claims, 5 Drawing Sheets

(51) Int. Cl.
   *B29C 64/124*   (2017.01)
   *A61K 6/887*    (2020.01)
   *A61K 6/17*     (2020.01)
   *C08F 222/10*   (2006.01)
   *C08K 3/36*     (2006.01)
   *C08K 9/02*     (2006.01)
   *B33Y 70/10*    (2020.01)
   *B33Y 80/00*    (2015.01)
   *B29K 509/02*   (2006.01)
   *B29L 31/00*    (2006.01)

(56) References Cited

U.S. PATENT DOCUMENTS

| | | | |
|---|---|---|---|
| 3,795,524 A | 3/1974 | Sowman | |
| 4,047,965 A | 9/1977 | Karst | |
| 4,307,219 A | 12/1981 | Larson | |
| 4,480,085 A | 10/1984 | Larson | |
| 4,642,126 A | 2/1987 | Zador | |
| 4,652,274 A | 3/1987 | Boettcher | |
| 4,737,593 A | 4/1988 | Ellrich | |
| 4,752,338 A | 6/1988 | Reiners et al. | |
| 4,954,462 A | 9/1990 | Wood | |
| 5,185,299 A | 2/1993 | Wood | |
| 5,427,835 A | 6/1995 | Morrison | |
| 5,780,154 A | 7/1998 | Okano | |
| 5,981,621 A | 11/1999 | Clark | |
| 6,183,593 B1 | 2/2001 | Narang | |
| 6,572,693 B1 | 6/2003 | Wu | |
| 6,624,211 B2 | 9/2003 | Karim | |
| 6,730,156 B1 | 5/2004 | Windisch | |
| 6,899,948 B2 | 5/2005 | Zhang | |
| 6,921,500 B1 | 7/2005 | Feenstra | |
| 8,329,776 B2 | 12/2012 | Hecht | |
| 8,389,599 B2 | 3/2013 | Yang | |
| 9,295,617 B2 | 3/2016 | Eckert | |
| 2010/0044895 A1 | 2/2010 | Sun et al. | |
| 2010/0105802 A1* | 4/2010 | Kuboe | A61K 6/76 523/116 |
| 2010/0292363 A1* | 11/2010 | Neffgen | A61K 6/887 977/773 |
| 2014/0131908 A1 | 5/2014 | Sun | |
| 2014/0150967 A1* | 6/2014 | Kurimura | B32B 17/1099 156/379.8 |
| 2014/0167300 A1 | 6/2014 | Lee | |
| 2015/0376476 A1 | 12/2015 | Rahim | |
| 2016/0009075 A1* | 1/2016 | Lefebvre | B41F 9/00 101/170 |
| 2016/0128909 A1 | 5/2016 | Fontein | |
| 2017/0007362 A1 | 1/2017 | Chen | |
| 2018/0326480 A1* | 11/2018 | Opschoor | B22F 3/1039 |
| 2020/0206092 A1* | 7/2020 | Herrmann | A61K 6/17 |

FOREIGN PATENT DOCUMENTS

| | | | |
|---|---|---|---|
| CN | 102223843 A | 10/2011 | |
| EP | 0562826 | 9/1993 | |
| EP | 2008636 | 12/2008 | |
| JP | 2004-238597 | 8/2004 | |
| JP | 2019-525967 A | 9/2019 | |
| WO | WO 1996-015179 | 5/1996 | |
| WO | WO 2001-030304 | 5/2001 | |
| WO | WO-0130306 A1 * | 5/2001 | ......... A61K 6/0017 |
| WO | WO 2014-098956 | 6/2014 | |
| WO | WO 2015-126666 | 8/2015 | |
| WO | WO 2015-200173 | 12/2015 | |
| WO | WO 2016-071811 | 5/2016 | |
| WO | WO 2017-036885 | 3/2017 | |
| WO | WO-2017036885 A1 * | 3/2017 | ......... A61K 6/0005 |
| WO | WO 2017-081160 | 5/2017 | |
| WO | WO-2017136374 A1 * | 8/2017 | ......... A61K 6/0005 |
| WO | 2017/207366 A1 | 12/2017 | |

OTHER PUBLICATIONS

Hintzer, "Fluoro(co)polymer, Organic" Ullmann's Encyclopedia of Industrial Chemisty, 7$^{th}$ Edition, 2013, Wiley-VCH Verlag Chemie, Weinheim, Germany. 55 pages.

International Search Report for PCT International Application No. PCT/IB2018/056371, dated Nov. 7, 2018, 6 pages.

* cited by examiner

RADIATION CURABLE COMPOSITIONS AND COMPOSITE ARTICLES MADE USING AN ADDITIVE MANUFACTURING PROCESS

CROSS REFERENCE TO RELATED APPLICATIONS

This application is a national stage filing under 35 U.S.C. 371 of PCT/IB2018/056371, filed Aug. 22, 2018, which claims the benefit of U.S. Application No. 62/556,649, filed Sep. 11, 2017, the disclosure of which is incorporated by reference in its/their entirety herein.

TECHNICAL FIELD

The present disclosure relates to composite articles and additive manufacturing processes for making such composite articles by selectively curing radiation curable compositions. More particularly, the processes use an additive manufacturing device to selectively cure the radiation curable composition to form a composite dental restoration.

BACKGROUND

Various dental restorations, for example, crowns, bridges, inlays, onlays, veneers, and pontics, are used in the practice of dentistry. Preformed dental restorations, for example dental crowns, may be manufactured in a factory, shipped in kits to dentists, and shaped or otherwise adapted chairside to create custom dental restorations. Metals such as stainless steel and aluminum have been the favored materials for such restorations, because they are strong, yet malleable. Thin wall stainless steel crowns, having a wall thickness of 150-200 microns, can be mass produced at low cost, require minimal removal of tooth structure, and can be trimmed and bent by the dentist at chair side to create a tight fitting and durable restoration. Unfortunately, tooth-like aesthetics are not usually possible with stainless steel, and attempts to substitute (co)polymers, like polycarbonate, for metals have yielded crowns with durability substantially less than steel crowns.

Ceramics, such as zirconia, may alternatively be used for fabrication of more aesthetic dental restorations, and may be pigmented or colored to match tooth color. These materials typically exhibit good durability, high strength and, in the case of zirconia, can be engineered to undergo transformation toughening to reduce the risk of brittle fracture. Because ceramic materials generally have low ductility and high hardness, the shape of the restoration is desirably custom created to precisely match the dentition of the individual patient.

Polymer-ceramic composites are alternative materials for restoring teeth. These materials may be pre-shaped in a dental laboratory or delivered to the dentist in a form that allows shaping and curing of the restoration in the mouth of the patient. The cured form of these materials offers lower strength than native tooth enamel, but the incorporation of high amounts of ceramic filler can result in restorations that exhibit wear resistance comparable to natural tooth structure.

SUMMARY

The art continually searches for new methods and materials for producing dental restorations. Accordingly, a need exists for new types of (co)polymer-ceramic materials, as well as new ways to process such materials into dental restorations.

Briefly, in one aspect, the present disclosure describes a radiation curable composition including at least one radiation hardenable component, a photo-initiator, and a filler material having a population of particulates in an amount greater than or equal to 50% by weight of the printable composition. The population of particulates exhibits a median diameter (D50) of greater than 0.3 micrometer on a volume-average basis as determined using the Particle Size Test Method, and the radiation curable composition exhibits a viscosity of less than 150 Pa·s when measured using the Viscosity Test Method.

In another aspect, the present disclosure describes a method for producing a composite article, the method including the steps of (a) providing a radiation curable composition including at least one radiation curable (e.g., radiation hardenable) component, a photo-initiator, and a filler material having a population of particulates in an amount greater than or equal to 50% by weight of the printable composition, wherein the population of particulates exhibits a median diameter (D50) of greater than 0.3 micrometer on a volume-average basis as determined using the Particle Size Test Method, further wherein the radiation curable composition exhibits a viscosity of less than 150 Pa·s when measured using the Viscosity Test Method, optionally wherein the radiation curable composition is substantially free of organic solvents; and (b) selectively exposing a portion of the radiation curable composition to a source of actinic radiation to at least partially cure the exposed portion of the radiation curable composition, thereby forming a hardened layer, wherein steps (a) and (b) are repeated to form a near net-shape composite article. The composite articles may include composite dental restorations, for example, dental crowns, bridges, inlays, onlays, veneers, pontics, or a combination thereof.

In a further aspect, the present disclosure describes a method for making a dental crown, the method including the steps of (a) receiving a design for a dental crown having a wall having a bottom edge, and an occlusal portion joined with the wall opposite the bottom edge, the wall and the occlusal portion forming an interior surface and an opposing exterior surface, wherein the wall and the occlusal portion both comprise an additively manufacturable material; and (b) making the dental crown using an additive manufacturing method. The additive manufacturing method includes the steps of (i) providing a radiation curable composition including at least one radiation curable (i.e., photocurable) component, a photo-initiator, and a filler material having a population of particulates in an amount greater than or equal to 50% by weight of the printable composition, wherein the population of particulates exhibits a median diameter (D50) of greater than 0.3 micrometer on a volume-average basis as determined using the Particle Size Test Method, further wherein the radiation curable composition exhibits a viscosity of less than 150 Pa·s when measured using the Viscosity Test Method; and (ii) selectively exposing a portion of the radiation curable composition to a source of actinic radiation to at least partially cure the exposed portion of the radiation curable composition, thereby forming a hardened layer. Steps (i) and (ii) are repeated to form the dental crown as a near net-shape composite article. Optionally the radiation curable composition is substantially free of organic solvents and/or polymerizable monomers.

In a yet another aspect, the present disclosure describes a stereo-photolithography apparatus including a vat; a radiation curable composition within the vat, a movable stage at least partially submerged in the radiation curable composition within the vat, and a source of actinic radiation adapted to selectively expose a portion of the radiation curable composition to the source of actinic radiation to at least partially cure the exposed portion of the radiation curable composition, thereby forming a hardened layer. The radiation curable composition includes at least one radiation hardenable component, a photo-initiator, and a filler material having a population of particulates in an amount greater than or equal to 50% by weight of the printable composition, wherein the population of particulates exhibits a median diameter (D50) of greater than 0.3 micrometer on a volume-average basis as determined using the Particle Size Test Method, further wherein the radiation curable composition exhibits a viscosity of less than 150 Pa·s when measured using the Viscosity Test Method. Optionally the radiation curable composition is substantially free of organic solvents and/or polymerizable monomers.

In still another aspect, the present disclosure describes a system including a display that displays a 3D model of a dental restoration, and one or more processors that, in response to the 3D model selected by a user, cause an additive manufacturing device to create a near net shape composite dental restoration using an additive manufacturing method. The additive manufacturing method includes the steps of (a) providing a radiation curable composition, and (b) selectively exposing a portion of the radiation curable composition to a source of actinic radiation to at least partially cure the exposed portion of the radiation curable composition, thereby forming a hardened layer. Steps (a) and (b) are repeated sequentially or continuously to form the near net-shape composite dental restoration. The radiation curable composition includes at least one radiation curable (e.g., radiation hardenable) component, a photo-initiator, and a filler material having a population of particulates in an amount greater than or equal to 50% by weight of the printable composition, wherein the population of particulates exhibits a median diameter (D50) of greater than 0.3 micrometer on a volume-average basis as determined using the Particle Size Test Method, further wherein the radiation curable composition exhibits a viscosity of less than 150 Pa·s when measured using the Viscosity Test Method.

In any of the foregoing aspects, the radiation curable composition is preferably substantially free of organic solvents and/or polymerizable monomers. Preferably, the at least one radiation hardenable component is an ethylenically-unsaturated material, which more preferably is selected from dimers, trimers, oligomers, and combinations thereof. Preferably, the photo-initiator is a photo-radical photo-initiator and not a cationic photo-initiator. Preferably, the filler material includes inorganic particulates, which may include a metal, a metal alloy, a metal oxide, a metal nitride, a metal carbide, carbon, and combinations thereof. In some embodiments, the inorganic particulates are surface treated.

Various unexpected results and advantages are obtained in exemplary embodiments of the disclosure. In exemplary embodiments, the compositions have a sufficiently low viscosity to permit their use in a wide range of additive manufacturing processes. In certain exemplary embodiments, the compositions of the present disclosure contain low or no volatile components, such as organic solvents or polymerizable monomers. In further exemplary embodiments, the compositions resist phase separation and/or settling of the filler material, and the compositions thus exhibit good shelf life and shelf stability, even for a period of four months or longer at 22° C.

In additional exemplary embodiments, the disclosure provides processes that permit the rapid production of composite articles with high fidelity to an original 3D model. The resulting composite articles, which may preferably be dental restorations, may be formed with a near net-shape, without substantial shrinkage or void formation, due to the substantial absence of volatile components such as organic solvents and monomers. The resulting composite articles may also exhibit a high Flexural Strength (e.g., at least 80 MPa) when subjected to the Flexural Strength Test. These and other unexpected results and advantages are within the scope of the following exemplary embodiments.

Listing of Exemplary Embodiments

1. A radiation curable composition comprising at least one radiation hardenable component, a photo-initiator, and a filler material comprising a population of particulates in an amount greater than or equal to 50% by weight of the printable composition, wherein the population of particulates exhibits a median diameter (D50) of greater than or equal to 0.3 micrometer on a volume-average basis as determined using the Particle Size Test Method, further wherein the radiation curable composition exhibits a viscosity of less than or equal to 150 Pa·s when measured using the Viscosity Test Method, optionally wherein the radiation curable composition is substantially free of organic solvents.

2. The radiation curable composition of Embodiment 1, wherein the at least one radiation hardenable component is ethylenically-unsaturated.

3. The radiation curable composition of Embodiment 1 or 2, wherein the at least one radiation hardenable component is selected from the group consisting of dimers, trimers, oligomers, and combinations thereof, optionally wherein the radiation curable composition is substantially free of polymerizable monomers.

4. The radiation curable composition of any one of Embodiments 1-3, wherein the photo-initiator is not a cationic photo-initiator.

5. The radiation curable composition of any one of Embodiments 1-4 wherein the photo-initiator is a photo-radical photo-initiator.

6. The radiation curable composition of any one of Embodiments 1-5, wherein the filler material comprises inorganic particulates.

7. The radiation curable composition of Embodiment 6, wherein the inorganic particulates comprise a metal, a metal alloy, a metal oxide, a metal nitride, a metal carbide, carbon, and combinations thereof.

8. The radiation curable composition of Embodiment 6 or 7, wherein the inorganic particulates are surface treated.

9. The radiation curable composition of any one of Embodiments 1-8, wherein the population of particulates comprises a nano-filler, optionally wherein the nano-filler comprises nano-clusters.

10. The radiation curable composition of any one of Embodiments 1-9, further comprising at least one additive selected from the group consisting of a solvent, a monomer, a (co)polymer, an emulsifier, a polymerization inhibitor, an absorption modifier, photosensitizer, a colorant, a fiber reinforcement material, or a combination thereof.

11. The radiation curable composition of any one of Embodiments 1-10, wherein the radiation curable composition does not undergo sedimentation or phase separation of the population of particulates after four months at 22° C.

12. A method for producing a composite article, the method comprising (a) providing a radiation curable composition further comprising at least one photocurable component, a photo-initiator, and a filler material comprising a population of particulates in an amount greater than or equal to 50% by weight of the printable composition, wherein the population of particulates exhibits a median diameter (D50) of greater than or equal to 0.3 micrometer on a volume-average basis as determined using the Particle Size Test Method, further wherein the radiation curable composition exhibits a viscosity of less than or equal to 150 Pa·s when measured using the Viscosity Test Method, optionally wherein the radiation curable composition is substantially free of organic solvents; and (b) selectively exposing a portion of the radiation curable composition to a source of actinic radiation to at least partially cure the exposed portion of the radiation curable composition, thereby forming a hardened layer, wherein steps (a) and (b) are repeated to form a near net-shape composite article.

13. The method of Embodiment 12, further comprising at least one of heating the radiation curable composition, removing uncured radiation curable composition from the near net-shape composite article, washing the near net-shape composite article with a solvent, or heating the near net-shape composite article.

14. A composite article prepared according to the method of any one of Embodiments 1-13.

15. The composite article of Embodiment 14, wherein the composite article exhibits a Flexural Strength of at least 80 MPa.

16. The composite article of Embodiments 14-15, wherein the composite article is a dental restoration selected from the group consisting of a crown, a bridge, an inlay, an onlay, a veneer, a pontic, or a combination thereof.

17. A method for making a near net-shape composite dental crown, comprising the steps of (a) receiving a design for a dental crown comprising a wall having a bottom edge, and an occlusal portion joined with the wall opposite the bottom edge, the wall and the occlusal portion forming an interior surface and an opposing exterior surface; and (b) making a composite dental crown using an additive manufacturing method, the method further comprising (i) providing a radiation curable composition further comprising at least one radiation hardenable component, a photo-initiator, and a filler material comprising a population of particulates in an amount greater than or equal to 50% by weight of the printable composition, wherein the population of particulates exhibits a median diameter (D50) of greater than 0.3 micrometer on a volume-average basis as determined using the Particle Size Test Method, further wherein the radiation curable composition exhibits a viscosity of less than 150 Pa·s when measured using the Viscosity Test Method, optionally wherein the radiation curable composition is substantially free of organic solvents; and (ii) selectively exposing a portion of the radiation curable composition to a source of actinic radiation to at least partially cure the exposed portion of the radiation curable composition, thereby forming a hardened layer, wherein steps (i) and (ii) are repeated to form the near net-shape composite dental crown.

18. A stereo-photolithography apparatus comprising a vat; a radiation curable composition within the vat, wherein the radiation curable composition further comprises at least one radiation hardenable component, a photo-initiator, and a filler material comprising a population of particulates in an amount greater than or equal to 50% by weight of the printable composition, wherein the population of particulates exhibits a median diameter (D50) of greater than 0.3 micrometer on a volume-average basis as determined using the Particle Size Test Method, further wherein the radiation curable composition exhibits a viscosity of less than 150 Pa·s when measured using the Viscosity Test Method, optionally wherein the radiation curable composition is substantially free of organic solvents; a movable stage at least partially submerged in the radiation curable composition within the vat; and a source of actinic radiation adapted to selectively expose a portion of the radiation curable composition to the source of actinic radiation to at least partially cure the exposed portion of the radiation curable composition, thereby forming a hardened layer.

19. A system comprising a display that displays a 3D model of a dental restoration; and one or more processors that, in response to the 3D model selected by a user, cause an additive manufacturing device to create a near net shape composite dental restoration using an additive manufacturing method, the additive manufacturing method comprising the steps of (a) providing a radiation curable composition further comprising at least one radiation hardenable component, a photo-initiator, and a filler material comprising a population of particulates in an amount greater than or equal to 50% by weight of the printable composition, wherein the population of particulates exhibits a median diameter (D50) of greater than 0.3 micrometer on a volume-average basis as determined using the Particle Size Test Method, further wherein the radiation curable composition exhibits a viscosity of less than 150 Pa·s when measured using the Viscosity Test Method, optionally wherein the radiation curable composition is substantially free of organic solvents; and (b) selectively exposing a portion of the radiation curable composition to a source of actinic radiation to at least partially cure the exposed portion of the radiation curable composition. thereby forming a hardened layer, wherein steps (a) and (b) are repeated sequentially or continuously to form the near net-shaped composite dental restoration.

Various aspects and advantages of exemplary embodiments of the disclosure have been summarized. The above Summary is not intended to describe each illustrated embodiment or every implementation of the present certain exemplary embodiments of the present disclosure. The Drawings and the Detailed Description that follow more particularly exemplify certain preferred embodiments using the principles disclosed herein.

BRIEF DESCRIPTION OF THE DRAWINGS

The disclosure may be more completely understood in consideration of the following detailed description of various embodiments of the disclosure in connection with the accompanying figures, in which.

Figure 1:
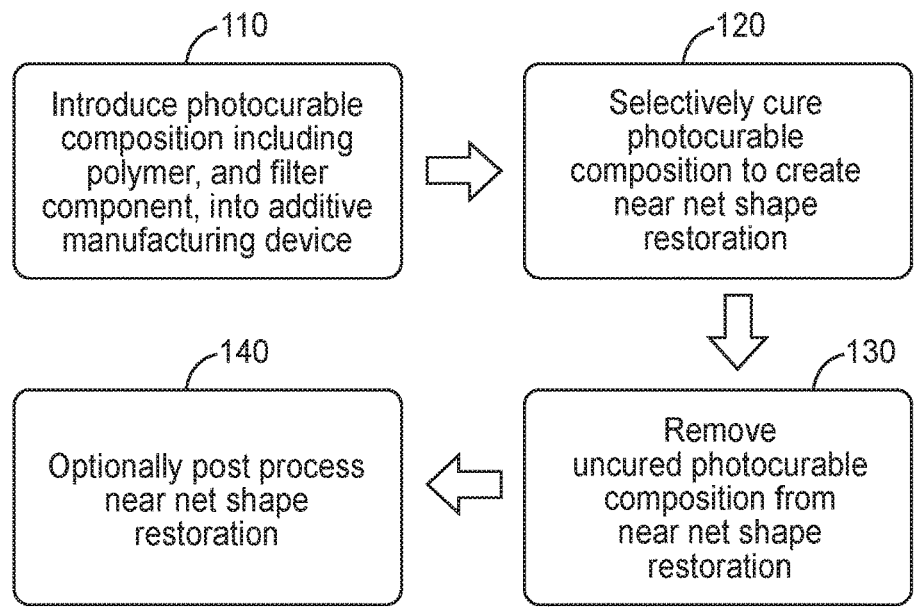
FIG. 1 is a flow chart of a method for making composite (co)polymer-ceramic dental restorations using additive manufacturing according to the present disclosure.

In the drawings, like reference numerals indicate like elements. While the above-identified drawing, which may not be drawn to scale, sets forth various embodiments of the present disclosure, other embodiments are also contemplated, as noted in the Detailed Description. In all cases, this disclosure describes the presently disclosed disclosure by way of representation of exemplary embodiments and not by express limitations. It should be understood that numerous other modifications and embodiments can be devised by those skilled in the art, which fall within the scope and spirit of this disclosure.

DETAILED DESCRIPTION

For the following Glossary of defined terms, these definitions shall be applied for the entire application, unless a different definition is provided in the claims or elsewhere in the specification.

Glossary

Certain terms are used throughout the description and the claims that, while for the most part are well known, may require some explanation. It should understood that as used herein:

The term "additive manufacturing" means processes used to make 3-dimensional articles by addition of material. An example of an additive manufacturing technique is stereophotolithography (SPLA) in which successive layers of material are laid down under computer control and are subsequently cured by radiation. The articles can be of almost any shape or geometry and are produced from a 3-dimensional model or other electronic data source. Other examples of additive manufacturing processes or techniques include 3d-printing.

The term "adjoining" with reference to a particular layer or structural feature means joined with or attached to another layer, in a position wherein the two layers are either next to (i.e., adjacent to) and directly contacting each other, or contiguous with each other but not in direct contact (i.e., there are one or more additional layers intervening between the layers).

The term "associated" with reference to a population comprising a plurality of particles refers to a grouping of two or more primary particles that are aggregated and/or agglomerated. Similarly, the term "non-associated" with reference to a population comprising a plurality of particles refers to two or more primary particles that are free or substantially free from aggregation and/or agglomeration.

The term "agglomerated" with reference to a population comprising a plurality of particles is descriptive of a weak association of particles usually held together by charge or polarity and can be broken down into smaller entities. Agglomerated fillers are commercially available e.g. from Degussa, Cabot Corp or Wacker under the product designation Aerosil™, CAB-O-SIL™ and HDK. Similarly, a "non-agglomerated filler" means that the filler particles are present in the resin in a discrete, un-associated (i.e. non-agglomerated and non-aggregated) stage. If desired this can be proven by Transmission Electron microscopy (TEM). Non-agglomerated nano-sized silicas are commercially available e.g. from Nalco Chemical Co. (Naperville, Ill.) under the product designation NALCO COLLOIDAL SILICAS e.g. NALCO products #1040, 1042, 1050, 1060, 2327 and 2329. Non-agglomerated fillers are used and described e.g. in EP 2 167 013 B1 (3M). The content of this reference is herewith incorporated by reference.

The term "aggregated" with reference to a population comprising a plurality of particles is descriptive of a strong association of particles often bound together by, for example, residual chemicals treatment or partially sintering. The specific surface of aggregated particles is typically smaller than the specific surface of the primary particles the aggregate is made of (cf. DIN 53206; 1972). Further breakdown of the aggregates into smaller entities may occur during a polishing step applied to the surface of a composition containing the aggregated filler but not during dispersing the aggregated particles in a resin. Aggregated fillers and processes for the production and surface treatment thereof are described e.g. in WO 01/30304 and U.S. Pat. No. 6,730,156 (3M). The content of these references is herewith incorporated by reference.

The terms "(co)polymer" or "(co)polymers" includes homopolymers and co(co)polymers, as well as homopolymers or co(co)polymers that may be formed in a miscible blend, e.g., by coextrusion or by reaction, including, e.g., transesterification. The term "co(co)polymer" includes random, block and star (e.g. dendritic) co(co)polymers.

The term "curing" means the hardening or partial hardening of a composition by any mechanism, e.g., by heat, light, radiation, e-beam, microwave, chemical reaction, or combinations thereof.

The term "cured" refers to a material or composition that has been hardened or partially hardened (e.g., (co)polymerized or crosslinked) by curing.

The term "glass" means an inorganic non-metallic amorphous material which is thermodynamically an under-cooled and frozen melt. Glass refers to a hard, brittle, transparent solid. Typical examples include soda-lime glass and borosilicate glass. A glass is an inorganic product of fusion which has been cooled to a rigid condition without crystallizing. Most glasses contain silica as their main component and a certain amount of glass former. The filler material or composite article described in the present disclosure typically does not contain a glass.

The term "glass-ceramic" means an inorganic non-metallic material where one or more crystalline phases are surrounded by a glassy phase so that the material comprises a glass material and a ceramic material in a combination or mixture. Thus, a glass ceramic is a material sharing many properties with both glass and more traditional crystalline ceramics. It is formed as a glass, and then made to crystallize partly by heat treatment. Glass ceramics may refer to a mixture of lithium-, silicon- and aluminium oxides.

The term "hardenable" refers to a material that can be cured or solidified, e.g., by causing (co)polymerization or cross-linking, more particularly radiation-induced (co)polymerization or cross-linking, or the like.

The term "median particle size" means the point on the cumulative particle diameter curve, plotted on a volume average basis, at which 50% of the particles are larger, and 50% of the particles are smaller, than the D50 diameter, as determined using Particle Size Test Method using laser diffraction particle size analysis, as defined herein below.

The term "(meth)acrylate" is a shorthand reference to acrylate, methacrylate, or combinations thereof, and "(meth) acrylic" is a shorthand reference to acrylic, methacrylic, or combinations thereof. As used herein, "(meth)acrylate-functional compounds" are compounds that include, among other things, a (meth)acrylate moiety.

The term "monomer" is any chemical substance which can be characterized by a chemical formula, bearing polymerizable groups (including (meth)acrylate groups) which can be polymerized to form oligomers or polymers thereby increasing the molecular weight. The molecular weight of monomers can usually simply be calculated based on the chemical formula given.

The term "nano-filler" means a filler, the individual particles thereof have a size in the region of nanometers, e.g. an average particle diameter of less than about 200 nm or less than about 100 nm or less than about 50 nm. Useful examples are given in U.S. Pat. No. 6,899,948/Zhang et al.) and U.S. Pat. No. 6,572,693 (Wu et al.). The content with regard to nano-sized silica particles is herein incorporated by reference. The measurement of the size of nano-particles is preferably based on a TEM (transmission electron microscopy) method, whereby a population is analyzed to obtain an average particle diameter. A preferred method for measuring the particle diameter can be described as follows: Samples with a thickness not exceeding 80 nm are placed on 200 mesh copper grids with carbon stabilized formvar substrates (SPI Supplies—a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200 KV. A population size of about 50-100 particles can be measured and an average diameter is determined.

The term "non-crosslinkable" refers to a (co)polymer that does not undergo cross-linking when exposed to actinic radiation or elevated heat. Typically, non-crosslinkable (co) polymers are non-functionalized (co)polymers such that they lack functional groups that would participate in cross-linking.

The term "nonreactive solvent" is a solvent that does not (co)polymerize into the radiation curable composition. As the solvent is nonreactive, it generally can be extracted from a printed (co)polymer-ceramic composite restoration according to methods discussed below without deleteriously affecting the material properties of the, e.g., high viscosity radiation hardenable component. Generally, nonreactive solvents are selected to be organic solvents.

The term "occlusal" means in a direction toward the outer tips of the patient's teeth; "facial" means in a direction toward the patient's lips or cheeks; and "lingual" means in a direction toward the patient's tongue.

The term "particle" or "particulate" means a substance being a solid having a shape which can be geometrically determined. The shape can be regular or irregular. Particles can typically be analysed with respect to e.g. particle size and particle size distribution. A particle can comprise one or more crystallites. Thus, a particle can comprise one or more crystal phases.

The term "photo-initiator" is used to describe a chemical substance being able to start or initiate the curing process of a (co)polymerizable composition upon exposure to radiation (e.g., a wavelength of 350 to 600 nm or 350 to 420 nm).

The term "powder" means a dry, bulk material composed of a large number of fine particles that may flow freely when shaken or tilted.

The term "primary particle size" refers to the size of a non-associated single crystal particle, which is considered to be a primary particle. X-ray diffraction (XRD) or Transmission Electron Microscopy (TEM) are typically used to measure the primary particle size.

The term "printable" means that a curable (i.e., hardenable) composition, prior to curing (i.e., hardening), has a viscosity profile consistent with the requirements and parameters of one or more additive manufacturing processes or systems.

The terms "radiation curable" and "radiation hardenable" are used synonymously, and for reference purposes herein, mean a curable or hardenable composition or component that can be at least partially cured (e.g., (co)polymerized or crosslinked) by exposure to a source of electromagnetic radiation to provide a composite article.

The term "resin" includes all radiation hardenable components (monomers, oligomers and/or (co)polymers) being present in a curable composition. The resin may contain only one radiation hardenable component compound or a mixture of different (co)polymerizable compounds.

The term "resin modified glass ionomer cement" means a hardenable dental material comprising acid-reactive glass, polyacid, water, polymerizable components and initiator. Resin modified glass ionomer cements undergo a twofold curing reaction, a glass ionomer acid base based cement reaction and polymerization of typically (methacrylate) acrylate based monomers.

The term "sol" means a dispersion of colloidal (i.e., particle diameter less than one micrometer) solid particles within a liquid.

The term "thermoplastic" refers to a (co)polymer that flows when heated sufficiently above its glass transition point and become solid when cooled.

The term "thermoset" refers to a (co)polymer that permanently sets upon curing and does not flow upon subsequent heating. Thermoset (co)polymers are typically cross-linked (co)polymers.

The terms "about" or "approximately" with reference to a numerical value or a shape means+/−five percent of the numerical value or property or characteristic, but expressly includes the exact numerical value. For example, a viscosity of "about" 1 Pa-sec refers to a viscosity from 0.95 to 1.05 Pa-sec, but also expressly includes a viscosity of exactly 1 Pa-sec. Similarly, a perimeter that is "substantially square" is intended to describe a geometric shape having four lateral edges in which each lateral edge has a length which is from 95% to 105% of the length of any other lateral edge, but which also includes a geometric shape in which each lateral edge has exactly the same length.

The terms "preferred" and "preferably" refer to embodiments of the disclosure that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure.

The term "substantially" with reference to a property or characteristic means that the property or characteristic is exhibited to a greater extent than the opposite of that property or characteristic is exhibited. For example, a substrate that is "substantially" transparent refers to a substrate that transmits more radiation (e.g. visible light) than it fails to transmit (e.g. absorbs and reflects). Thus, a substrate that transmits more than 50% of the visible light incident upon its surface is substantially transparent, but a substrate that transmits 50% or less of the visible light incident upon its surface is not substantially transparent.

By using terms of orientation such as "atop", "on", "over," "covering", "uppermost", "underlying" and the like for the location of various elements in the disclosed coated (co)polymer-ceramic composite restorations, we refer to the relative position of an element with respect to a horizontally-disposed, upwardly-facing substrate. However, unless otherwise indicated, it is not intended that the substrate or (co)polymer-ceramic composite restorations should have any particular orientation in space during or after manufacture.

By using the term "overcoated" to describe the position of a layer with respect to a substrate or other element of a (co)polymer-ceramic composite restoration of the present disclosure, we refer to the layer as being atop the substrate or other element, but not necessarily contiguous to either the substrate or the other element.

By using the term "separated by" to describe the position of a layer with respect to other layers, we refer to the layer as being positioned between two other layers but not necessarily contiguous to or adjacent to either layer.

As used in this specification and the appended embodiments, the singular forms "a", "an", and "the" include plural referents unless the content clearly dictates otherwise. Thus, for example, reference to fine fibers containing "a compound" includes a mixture of two or more compounds.

As used in this specification and the appended embodiments, the term "or" is generally employed in its sense including "and/or" unless the content clearly dictates otherwise.

As used in this specification, the recitation of numerical ranges by endpoints includes all numbers subsumed within that range (e.g. 1 to 5 includes 1, 1.5, 2, 2.75, 3, 3.8, 4, and 5).

Unless otherwise indicated, all numbers expressing quantities or ingredients, measurement of properties and so forth used in the specification and embodiments are to be understood as being modified in all instances by the term "about." Accordingly, unless indicated to the contrary, the numerical parameters set forth in the foregoing specification and attached listing of embodiments can vary depending upon the desired properties sought to be obtained by those skilled in the art utilizing the teachings of the present disclosure. At the very least, and not as an attempt to limit the application of the doctrine of equivalents to the scope of the claimed embodiments, each numerical parameter should at least be construed in light of the number of reported significant digits and by applying ordinary rounding techniques.

Exemplary embodiments of the present disclosure may take on various modifications and alterations without departing from the spirit and scope of the present disclosure. Accordingly, it is to be understood that the embodiments of the present disclosure are not to be limited to the following described exemplary embodiments, but is to be controlled by the limitations set forth in the claims and any equivalents thereof.

Various exemplary embodiments of the disclosure will now be described with particular reference to the Drawings. Exemplary embodiments of the present disclosure may take on various modifications and alterations without departing from the spirit and scope of the disclosure. Accordingly, it is to be understood that the embodiments of the present disclosure are not to be limited to the following described exemplary embodiments, but are to be controlled by the limitations set forth in the claims and any equivalents thereof Radiation Curable Compositions The disclosure describes radiation curable composition useful in producing near net shape (co)polymer-ceramic composite dental restorations using an additive manufacturing apparatus process (e.g., stereo-photolithography), as described further below. Thus in one illustrative embodiment, the present disclosure describes a radiation curable composition including at least one radiation hardenable component, a photo-initiator, and a filler material having a population of particulates in an amount greater than or equal to 50% by weight of the printable composition. The population of particulates exhibits a median diameter (D50) of greater than 0.3 micrometer on a volume-average basis as determined using the Particle Size Test Method, and the radiation curable composition exhibits a viscosity of less than 150 Pas when measured using the Viscosity Test Method.

Radiation curable compositions described herein can be mixed by known techniques. In some embodiments, for instance, a method for the preparation of a radiation curable composition described herein comprises the steps of mixing all or substantially all of the components of the radiation curable composition, heating the mixture, and optionally filtering the heated mixture. Softening the mixture, in some embodiments, is carried out at a temperature in a range of about 30° C. to about 85° C., more preferably about 35-50° C. or even 35-40° C. In some embodiments, a radiation curable composition described herein is produced by placing all or substantially all components of the composition in a reaction vessel and heating the resulting mixture to a temperature ranging from about 30° C. to about 85° C., more preferably about 35-50° C. or even 35-40° C., with stirring. The heating and stirring are continued until the mixture attains a substantially homogenized state.

Radiation curable compositions described herein can also exhibit a variety of desirable properties, non-cured, as green bodies, and as post-cured (co)polymer-ceramic composite restorations. A radiation curable composition, when non-cured, may advantageously have a viscosity profile consistent with the requirements and parameters of one or more additive manufacturing systems, as described further below. In some embodiments, the radiation curable composition exhibit good shelf stability, and do not undergo sedimentation or phase separation of the population of particulates even after four months at 22° C.

Radiation Hardenable Component

The radiation curable compositions of the present disclosure include at least one radiation hardenable component or radiation curable component. In some embodiments, for instance, radiation curing comprises selectively irradiating the radiation hardenable component with a source of actinic radiation having sufficient energy to initiate a (co)polymerization or cross-linking reaction. For instance, in some embodiments, ultraviolet (UV) radiation, e-beam radiation, or both, can be used as a source of actinic radiation. In other embodiments, gamma rays may be used as a radiation source.

Suitable radiation hardenable components are preferably ethylenically unsaturated, that is, they contain at least one ethylenically unsaturated bond, and are capable of under-going addition or free radical (co)polymerization. In some exemplary embodiments, the at least one radiation hardenable component is selected from the group consisting of dimers, trimers, oligomers, and combinations thereof. Preferably, the radiation curable composition is substantially free of monomers.

In certain embodiments, the radiation hardenable component has a molecular weight of 10,000 grams per mole or less, 9,000 g/mol or less, 8,000 g/mol or less, 7,000 g/mol or less, 6,000 g/mol or less, or 5,000 g/mol or less. Including a radiation hardenable component with such molecular weights can assist in providing a radiation curable composition that has a sufficiently low viscosity for use with vat (co)polymerization methods. Moreover, using a radiation hardenable component (e.g., monomer and/or oligomer) with a low molecular weight increases the ease with which the radiation hardenable component can interpenetrate the (co)polymer in solution to provide an integral (co)polymer-ceramic composite restoration upon (co)polymerization of the radiation hardenable component. Further, in select embodiments the radiation hardenable component is soluble or dispersible in water.

The radiation hardenable component is included in the radiation curable composition in an amount of 5 to less than 50 wt. % based on the total weight of the radiation curable composition, such as 5 to 25 wt. %, inclusive. Typically, the radiation hardenable component is included in the radiation curable composition in an amount of 5 wt. % or more, 7 wt. % or more, 5 wt. % or more, 10 wt. % or more, 12 wt. % or more, or 15 wt. % or more; and 50 wt. % or less, 45 wt. % or less, 40 wt. % or less, 35 wt. % or less, 30 wt. % or less, 25 wt. % or less, or 20 wt. % or less, based on the total weight of the radiation curable composition.

Photo-Initiator

Radiation curable compositions described herein further comprise one or more photo-initiators. Preferably, the photo-initiator is not a cationic photo-initiator. More preferably, the photo-initiator is a photo-radical photo-initiator. The photo-initiator is typically present in an amount from 0.1 to 5 or from 0.2 to 4 or from 0.5 to 3 wt. %.

In certain embodiments the photo-initiator(s) can be characterized by at least one or more, sometimes all of the following parameters:
  showing a radiation absorption band within a range from 200 to 500 or from 300 to 450 nm;
  having a slightly yellowish color.

The photo-initiator should be able to start or initiate the curing or hardening reaction of the radiation curable component(s) being present in the curable composition. The photo-initiator typically shows a light absorption band in a wave length range from 300 to 450 nm, preferably in the range from 350 to 420 nm.

Suitable photo-initiators are those available under the trade designations IRGACURE and DAROCUR from BASF (Ludwigshafen, Germany) and include 1-hydroxycyclohexyl phenyl ketone (IRGACURE 184), 2,2-dimethoxy-1,2-diphenylethan-1-one (IRGACURE 651), bis(2,4,6 trimethylbenzoyl)phenylphosphineoxide (IRGACURE 819), 1-[4-(2-hydroxyethoxy)phenyl]-2-hydroxy-2-methyl-1-propane-1-one (IRGACURE 2959), 2-benzyl-2-dimethylamino-1-(4-morpholinophenyl)butanone (IRGACURE 369), 2-methyl-1-[4-(methylthio)phenyl]-2-morpholinopropan-1-one (IRGACURE 907), Oligo[2-hydroxy-2-methyl-1-[4-(1-methylvinyl)phenyl]propanone] ESACURE ONE (Lamberti S.p.A., Gallarate, Italy), 2-hydroxy-2-methyl-1-phenyl propan-1-one (DAROCUR 1173), 2,4,6-trimethyl-benzoyldiphenylphosphine oxide (IRGACURE TPO), and 2,4,6-trimethylbenzoylphenyl phosphinate (IRGACURE TPO-L).

Additional suitable photo-initiators include for example and without limitation, benzyl dimethyl ketal, 2-methyl-2-hydroxypropiophenone, benzoin methyl ether, benzoin isopropyl ether, anisoin methyl ether, aromatic sulfonyl chlorides, photoactive oximes, and combinations thereof.

In some exemplary embodiments, it may be preferred to use a photo-initiator comprising a phosphine oxide moiety. Examples of such photo-initiators include the class of acylphosphine oxides, as described in e.g. in U.S. Pat. No. 4,737,593. Such acylphosphine oxides are of the general formula

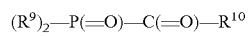

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S-, O-, or N-containing five- or six-membered heterocyclic group, or a —Z—C(=O)—P(=O)—$(R^9)_2$ group, wherein Z represents a divalent hydrocarbyl group such as alkylene or phenylene having from 2 to 6 carbon atoms.

Preferred acylphosphine oxides are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is bis(2,4,6-trimethylbenzoyl)phenyl phosphine oxide (IRGACURE™ 819, Ciba Specialty Chemicals, Tarrytown, N.Y.).

Tertiary amine reducing agents may be used in combination with an acylphosphine oxide. Illustrative tertiary amines include ethyl 4-(N,N-dimethylamino)benzoate and N,N-dimethylaminoethyl methacrylate.

Commercially-available phosphine oxide photo-initiators capable of free-radical initiation when irradiated at wavelengths of greater than 400 nm to 1,200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4-morpholinophenyl)-1-butanone (IRGACURE™ 369, Ciba Specialty Chemicals), bis(η5-2,4-cyclopentadien-1-yl)-bis(2,6-difluoro-3-(1H-pyrrol-1-yl)phenyl) titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.), 2,4,6-trimethyl-benzoyldiphenyl-phospine oxide (LUCIRIN™ TPO).

The photo-initiator can be present in a radiation curable composition described herein in any amount according to the particular constraints of the additive manufacturing process. In some embodiments, a photo-initiator is present in a radiation curable composition in an amount of up to about 5% by weight, based on the total weight of the radiation curable composition. In some cases, a photo-initiator is present in an amount of about 0.1-5% by weight, based on the total weight of the radiation curable composition. The photo-initiator(s) is typically present in the following amounts:

Lower amount: at least 0.01 or at least 0.05 or at least 0.1 wt. %;

Upper amount: at most 3 or at most 2 or at most 1.5 wt. %;

Range: from 0.01 to 3 or from 0.05 to 2 wt. % or 0.1 to 1.5 wt. %; wt. % with respect to the weight of the whole composition.

Filler Material

Radiation curable compositions described herein, further comprise a filler material comprising a population of particulates in an amount greater than or equal to 50% by weight of the printable composition. The population of particulates exhibits a median diameter (D50) of greater than or equal to 1 micrometer on a volume-average basis as determined using laser diffraction particle size analysis, as described herein below. The amount and median diameter of filler used in the radiation curable composition may have an impact on the viscosity of the curable composition, the abrasion resistance of the cured composition, or both.

The population of particulates is typically present in either of the following amounts:

Lower amount: at least 50%, 55%, 60%, or even 70% by weight of the printable composition;

Higher amount: at most 80%, 75%, 70%, or even 65% or 55% by weight of the printable composition;

Range: from 50% to 80%, inclusive, 50% to 75%, inclusive, or 50% to 65% by weight of the printable composition.

In presently-preferred embodiments, the filler material includes or may be entirely comprised of inorganic particulates. The inorganic particulates may include a metal, a metal alloy, a metal oxide, a metal nitride, a metal carbide, carbon, and combinations thereof. In certain exemplary embodiments, at least a portion of the inorganic particulates may be advantageously surface treated, as described further below.

In some exemplary embodiments, the inorganic filler material may comprise fumed silica. The specific surface of the hydrophobic fumed silica is typically from 100 to 300 or from 150 to 250 $m^2/g$. A mixture of different fumed silica can be used, if desired. For example, a mixture of fumed silica the surface of which has been treated with a hydrophobic surface treating agent and fumed silica the surface of which has been treated with a hydrophilic surface treating agent can be used.

Suitable hydrophobic surface-treating agents include: —$OSiR_3$, with R being selected from $C_{1-4}$ alkyl, preferably methyl and mixtures thereof. Hydrophobic fumed silica is also commercially available under the trade designations HDK, in particular HDK-H 2000 (Wacker), or Aerosil™ R812 (Evonik).

It has been found that using fumed silica the surface of which has been treated with surface treating agents containing polymerizable moieties, like (meth)acrylsilanes, may sometimes lead to a non-desired thickening of the curable composition, which may make the curable composition less suitable as processing material in an additive manufacturing process. However, according to one exemplary embodiment, the curable composition does not typically contain fumed silica having been surface treated with surface treating agents containing polymerizable moieties like (meth)acrylsilanes, in an amount of more than 2 wt. % or more than 1.5 wt. % or more than 1 wt. %.

If present, fumed silica is typically present in either of the following amounts:

Lower amount: at least 0.5 or at least 1 or at least 1.5 wt. %;

Higher amount: utmost 8 or utmost 7 or utmost 5 wt. %;

Range: from 0.5 to 8 or from 1 to 7 or from 1.5 to 5 wt. %; wt. % with respect to the weight of the whole curable composition.

In certain exemplary embodiments, the population of particulates may include a nano-filler. Optionally, the nano-filler comprises nano-cluster(s). One or more different kinds of nano-cluster(s) can be present. It has been found that compared to other fillers, using nano-cluster(s) can be beneficial because it allows for the formulation of a composition with high filler load resulting in better mechanical properties, e.g. polishability or abrasion and in higher aesthetics. The nano-cluster, if present, can typically be characterized by at least one or all of the following features:

Specific surface area: from 30 to 400 or from 60 to 300 or from 80 to 250 $m^2/g$, comprising particles of $SiO_2$, $ZrO_2$, $Al_2O_3$ and mixtures thereof.

If desired, the specific surface area of the nano-cluster can be determined according to the method of Brunauer, Emmet and Teller (BET), using a measurement device (e.g., Monosorb™) available from Quantachrome Instruments (Boynton Beach, Fla.).

A suitable nano-filler comprising aggregated nano-sized particles can be produced according to the processes described e.g. in U.S. Pat. No. 6,730,156 (preparatory example A). A useful nano-filler comprising aggregated nano-sized particles can be prepared from a suitable sol and one or more oxygen containing heavy metal compound solution(s) precursors which may be salts, sols, solutions, or nano-sized particles; of these, sols are preferred.

The solid particles are typically denser than the surrounding liquid and small enough so that the dispersion forces are greater than the gravitational force. In addition, the particles are of a size small enough so that they generally do not refract visible light. Judicious choice of the precursor sols leads to desired degree of visual opacity, strength etc.

Factors that will guide the choice of the sol depends on the combination of the following properties: a) the average size of the individual particles, which is preferably less than 100 nm in diameter, b) the acidity: the pH of the sol should be preferably below 6 and more preferably below 4, and c) the sol should be free of impurities that cause undue aggregation (during the filler preparation process) of the individual discrete particles, during the subsequent steps such as spray drying or calcining, into larger size particles that cannot be easily dispersed or commuted and hence decrease the translucency and polishability of a dental restoration made out of a composite comprising such nanoparticles.

If the starting sol is basic, it should be acidified e.g. by addition of nitric or other suitable acid to decrease the pH. However, choosing a basic starting sol is less desirable since it requires an additional step and may lead to the introduction of undesired impurities. Typical impurities that are preferably avoided are metal salts, particularly salts of alkaline metals e.g. sodium.

The non-heavy metal sol and heavy metal oxide precursors are mixed together preferably at a molar ratio to match the index of refraction of the hardenable resin. This imparts a low and desirable visual opacity. Preferably, the molar ratio ranges of non-heavy metal oxide ("non-HMO") to heavy metal oxide ("HMO"), expressed as non-HMO:HMO is 0.5:1 to 10:1, more preferably 3:1 to 9:1, and most preferable 4:1 to 7:1.

In one exemplary embodiment where the aggregated nano-sized particles contain silica and zirconium containing compounds, the method of preparation starts with a mixture of silica sol and zirconyl acetate, at about a 5.5:1 molar ratio. Prior to mixing the non-heavy metal oxide sol with the heavy metal oxide precursor, the pH of the non-heavy metal oxide sol is preferably reduced to provide an acidic solution having a pH of 1.5 to 4.0. The non-heavy metal oxide sol is then slowly mixed with the solution containing the heavy metal oxide precursor and vigorously agitated. Strong agitation is preferably performed throughout the blending process. The solution is then dried to remove the water and other volatile components. Drying can be accomplished in various ways, including for example, tray drying, fluidized bed and spray drying. In the preferred method where zirconyl acetate is used, drying by means of spray drying.

The resulting dried material is preferably made up of small substantially spherical particles as well as broken hollow spheres. These fragments are then batch calcined to further remove residual organics. The removal of the residual organics allows the filler to become more brittle, which results in more efficient particle size reduction. During calcining, the soak temperature is preferably set at 200° C. to 800° C., more preferably 300° C. to 600° C. Soaking is performed for 0.5 hours to 8 hours, depending on the amount of material being calcined. It is generally preferred that the soak time of the calcine step be such that a plateaued surface area is obtained. It is generally preferred that the time and temperature be chosen such that the resulting filler is white in color, free from black, grey, or amber colored particles, as determined by visual inspection.

The calcined material is then preferably milled to a median particle size of less than 5 μm, preferably less than 2 μm (on a volumetric basis), as can be determined by using a Sedigraph 5100 (Micrometrics, Norcross, Ga.). The particle size determination can be performed by first obtaining the specific density of the filler using an Accuracy 1330 Pycometer (Micrometrics, Norcross, Ga.). Milling can be accomplished by various methods including for example, stirred milling, vibratory milling, fluid energy milling, jet milling and ball milling. Ball milling is generally the preferred method.

The resulting fillers comprise, contain, consist essentially or consist of aggregated nano-sized particles. If desired, this can be proven by transmission electron microscopy (TEM). If desired, the surface of the filler particles can be surface treated. The surface-treatment can be accomplished according to a process as described in U.S. Pat. No. 6,730,156 (Windisch et al.) or U.S. Pat. No. 6,730,156 (Wu et al.). The content of these references is herewith incorporated by reference.

Once dispersed in the resin, the filler remains in an aggregated stage. That is, during the dispersion step the particles do not break up into discrete (i.e. individual) and un-associated (i.e. non-aggregated) particles.

If present, the nano-cluster(s) is typically present in either of the following amounts:
  Lower amount: at least 5 or at least 10 or at least 15 wt. %;
  Higher amount: utmost 40 or utmost 38 or utmost 35 wt. %;
  Range: from 5 to 40 or from 10 to 38 or from 15 to 35 wt. %; wt. % with respect to the weight of the whole curable composition.

The curable composition may, in some exemplary embodiments, also comprise x-ray visible particles. Adding x-ray visible particles to the dental composition is beneficial in that it enables the practitioner to better identify the material if placed in the mouth of a patient and distinguish between sound dental tooth structure and the artificial material. The material becomes radiopaque.

Suitable x-ray visible particles include particles of metal oxides and metal fluorides. Oxides or fluorides of heavy metals having an atomic number greater than about 28 can be preferred. The heavy metal oxide or fluoride should be chosen such that undesirable colors or shading are not imparted to the hardened resin in which it is dispersed. For example, iron and cobalt would not be favoured, as they impart dark and contrasting colors to the neutral tooth color of the dental material.

More preferably, the heavy metal oxide or fluoride is an oxide or fluoride of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof.

Suitable metal fluorides are e.g. yttrium trifluoride and ytterbium trifluoride. Most preferably, the oxides and fluorides of heavy metals having an atomic number greater than 30, but less than 72 are optionally included in the materials of the invention. Particularly preferred radiopacifying metal oxides include lanthanum oxide, zirconium oxide, yttrium oxide, ytterbium oxide, barium oxide, strontium oxide, cerium oxide, and combinations thereof. Other suitable fillers to increase radiopacity are salts of barium and strontium especially strontium sulphate and barium sulphate.

If present, x-ray visible particles are typically present in an amount from 0.1 to 20 or from 1 to 15 or from 2 to 10 wt. % with respect to the weight of the whole composition.

Optional Components

Various additional components may optionally be included in the radiation curable composition. Thus in some exemplary embodiments, the radiation curable composition includes at least one additive selected from the group consisting of a solvent, a monomer, a (co)polymer, an emulsifier, a polymerization inhibitor, an absorption modifier, a photosensitizer, a colorant, a fiber reinforcement material, or a combination thereof.

In some exemplary embodiments, the heavy metal oxide or metal fluoride particles may be surface treated.

Optional Solvent(s)

Although not presently preferred, the radiation curable compositions of the present disclosure may optionally include at least one solvent, preferably a nonreactive organic solvent. The viscosity of the radiation hardenable component can be significantly reduced by diluting the component in a solvent, such as a nonreactive solvent. Nonreactive solvents useful in the present disclosure are referred to herein as temporary solvents.

In certain embodiments, the temporary solvent is advantageously water, an inexpensive and environmentally friendly solvent. Alternatively, the temporary solvent may be an organic solvent having a boiling point of at least 50° C. The boiling point is often at least 100° C., at least 200° C., and typically no greater than 300° C. Suitable temporary solvent are typically non-volatile at ambient temperatures (20-25° C.) and have vapor pressures below about 150.0 hPa at 20° C. (preferably, below about 15.0 hPa at 20° C.; more preferably, below about 1.5 hPa at 20° C.; most preferably, below about 0.15 hPa at 20° C.). Temporary solvents demonstrating the above properties can typically be retained in the radiation curable composition during the printing process even at elevated temperatures, yet be removed from the printed (co)polymer-ceramic composite restoration using conventional techniques such as vacuum assisted evaporation.

In certain exemplary embodiments, the temporary solvent can include one or more of water, propylene carbonate, methanol, isopropyl alcohol, and tripropylene glycol methyl ether (TPM), ethanol, acetone, ethyl acetate, methyl ethyl ketone, and mixtures thereof.

The temporary solvent is included in the radiation curable composition in an amount of 10 to 80 wt. %, inclusive, based on the total weight of the radiation curable composition, such as 25 to 60 wt. %, inclusive. Typically, the radiation hardenable component is included in the radiation curable composition in an amount of 10 wt. % or more, 12 wt. % or more, 15 wt. % or more, 17 wt. % or more, 20 wt. % or more, 22 wt. % or more, or 25 wt. % or more; and 80 wt. % or less, 75 wt. % or less, 70 wt. % or less, 65 wt. % or less, 60 wt. % or less, 55 wt. % or less, or 50 wt. % or less, based on the total weight of the radiation curable composition. Under certain conditions, a radiation curable composition having less than 10 wt. % temporary solvent may not have a viscosity suitable for vat (co)polymerization, in that the viscosity of radiation hardenable component is not adequately low. Conversely, a radiation curable composition including more than 80 wt. % temporary solvent can, under certain conditions, result in green bodies with insufficient green strength and may result in difficulties in adequately removing the temporary solvent from the printed (co)polymer-ceramic composite restoration.

Optional Monomer(s)

Although not presently preferred, one or more monomers may optionally be incorporated into the Such free-radically (co)polymerizable materials include mono-, di-, tri-, or other poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, the diurethane dimethacrylate called UDMA (mixture of isomers, e.g., Röhm Plex 6661-0) being the reaction product of 2-hydroxyethyl methacrylate (HEMA) and 2,2,4-trimethylhexamethylene diisocyanate (TMDI), glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200-500, co(co)polymerizable mixtures of acrylated monomers such as those in U.S. Pat. No. 4,652,274 (Boettcher et al.), and acrylated oligomers such as those of U.S. Pat. No. 4,642,126 (Zador et al.); polyfunctional (meth) acrylates comprising urethane, urea or amide groups, as those of EP2008636 (Hecht et al.). The radiation hardenable component optionally includes urethane groups, epoxy groups, or both. The radiation hardenable component also may comprise silicone acrylate oligomers, epoxy (meth) acrylate oligomers, polyester (meth)acrylate oligomers or chlorinated polyester (meth)acrylates, allylic oligomers and (meth)acrylic oligomers. Mixtures of two or more of these free radically (co)polymerizable materials can be used if desired.

The radiation hardenable component preferably comprises one or more poly(meth)acrylates, for example, di-, tri-, tetra- or pentafunctional monomeric or oligomeric aliphatic, cycloaliphatic or aromatic acrylates or methacrylates. For example, the radiation hardenable component can include polyfunctional urethane acrylates or urethane methacrylates. These urethane (meth)acrylates are known to the person skilled in the art and can be prepared in a known manner by, for example, reacting a hydroxyl-terminated polyurethane with acrylic acid or methacrylic acid, or by reacting an isocyanate-terminated pre(co)polymer with hydroxyalkyl (meth)acrylates to give the urethane (meth) acrylate. Suitable processes are disclosed, inter alia, in U.S. Pat. No. 8,329,776 (Hecht et al.) and U.S. Pat. No. 9,295,617 (Cub et al.). Suitable urethante methacrylates can include PEGDMA (polyethyleneglycol dimethacrylate having a molecular weight of approximately 400), aliphatic urethane methacrylates, aliphatic polyester urethane methacrylates, aliphatic polyester triurethane acrylates.

Examples of suitable aliphatic poly(meth)acrylates having more than two (meth)acrylate groups in their molecules are the triacrylates and trimethacrylates of hexane-2,4,6-triol; glycerol or 1,1,1-trimethylolpropane; ethoxylated or propoxylated glycerol or 1,1,1-trimethylolpropane; and the hydroxyl-containing tri(meth)acrylates which are obtained by reacting triepoxide compounds, for example the triglycidyl ethers of said triols, with (meth)acrylic acid. It is also possible to use, for example, pentaerythritol tetraacrylate, bistrimethylolpropane tetraacrylate, pentaerythritol monohydroxytriacrylate or -methacrylate, or dipentaerythritol monohydroxypentaacrylate or -methacrylate.

Another suitable class of free radical (co)polymerizable compounds includes aromatic di(meth) acrylate compounds and trifunctional or higher functionality (meth) acrylate compound. Trifunctional or higher functionality meth(acrylates) can be tri-, tetra- or pentafunctional monomeric or oligomeric aliphatic, cycloaliphatic or aromatic acrylates or methacrylates.

Examples of suitable aliphatic tri-, tetra- and pentafunctional (meth)acrylates are the triacrylates and trimethacrylates of hexane-2,4,6-triol; glycerol or 1,1,1-trimethylolpropane; ethoxylated or propoxylated glycerol or 1,1,1-trimethylolpropane; and the hydroxyl-containing tri(meth) acrylates which are obtained by reacting triepoxide compounds, for example the triglycidyl ethers of said triols, with (meth)acrylic acid. It is also possible to use, for example, pentaerythritol tetraacrylate, bistrimethylolpropane tetraacrylate, pentaerythritol monohydroxytriacrylate or -methacrylate, or dipentaerythritol monohydroxypentaacrylate or -methacrylate. In some embodiments, tri(meth)acrylates comprise 1,1-trimethylolpropane triacrylate or methacrylate, ethoxylated or propoxylated 1,1,1-trimethylolpropanetriacrylate or methacrylate, ethoxylated or propoxylated glycerol triacrylate, pentaerythritol monohydroxy triacrylate or methacrylate, or tris(2-hydroxy ethyl) isocyanurate triacrylate. Further examples of suitable aromatic tri(meth)acrylates are the reaction products of triglycidyl ethers of trihydroxy benzene and phenol or cresol novolaks containing three hydroxyl groups, with (meth) acrylic acid.

In some cases, a radiation hardenable component comprises diacrylate and/or dimethacrylate esters of aliphatic, cycloaliphatic or aromatic diols, including 1,3- or 1,4-butanediol, neopentyl glycol, 1,6-hexanediol, diethylene glycol, triethylene glycol, tetraethylene glycol, polyethylene glycol, tripropylene glycol, ethoxylated or propoxylated neopentyl glycol, 1,4-dihydroxymethylcyclohexane, 2,2-bis (4-hydroxycyclohexyl)propane or bis(4-hydroxycyclohexyl)methane, hydroquinone, 4,4'-dihydroxybiphenyl, bisphenol A, bisphenol F, bisphenol S, ethoxylated or propoxylated bisphenol A, ethoxylated or propoxylated bisphenol F or ethoxylated or propoxylated bisphenol S. In some cases, a radiation hardenable component of a radiation curable composition described herein comprises one or more higher functional acrylates or methacrylates such as dipentaerythritol monohydroxy pentaacrylate or bis(trimethylolpropane)tetraacrylate.

Optional (Co)Polymer(s)

Although not presently preferred, the radiation curable compositions of the present disclosure may optionally include at least one (co)polymer. The at least one (co)polymer may provide flexibility to the final (co)polymer-ceramic composite restoration (e.g., at least a minimum elongation at break). In some embodiments, the (co)polymer comprises a non-crosslinkable (co)polymer. Inclusion of a non-crosslinkable (co)polymer can be advantageous because when the radiation curable composition is exposed to actinic radiation to (co)polymerize the radiation hardenable component, the (co)polymer does not crosslink and decrease its elongation capability.

Alternatively, in some embodiments the (co)polymer comprises one or more functional groups selected from hydroxyl groups, carboxyl groups, amino groups, and siloxane groups. These functional groups can be reactive with other components of the radiation curable composition during printing, such as the (co)polymerizable composition. Inclusion of a (co)polymer having at least one functional group can be advantageous because it can be desirable to attach the (co)polymer to the radiation hardenable component to assist in maintaining their interpenetration following printing. In some embodiments, the (co)polymer comprises a thermoplastic (co)polymer. Inclusion of a thermoplastic (co)polymer can be advantageous because the (co)polymer is able to soften or melt with heat and be formed into different shapes without damaging the (co)polymer chains.

Typically, the (co)polymer comprises a weight average molecular weight of at least 5,000 grams per mole and no greater than 20,000 grams per mole (g/mol), 15,000 g/mol 10,000 g/mol, 7,500 g/mol, or even 6,000 g/mol. The weight average molecular weight may be measured by gel permeation chromatography (GPC) using a light scattering detector providing an absolute molecular weight without resorting to use of standard having known molecular weight. The use of (co)polymers having a weight average molecular weight of 20,000 g/mol or less may tend to provide a final (co)polymer-ceramic composite restoration having at least a certain desirable minimum elongation at break.

Suitable (co)polymers include for instance and without limitation, polyethylene (PE), poly(meth)acrylate, polypropylene, polyurethane, sulfopolyester, polycarbonate, polyethylene terephthalate (PET), a thermoplastic fluoro(co)polymer, and combinations thereof. In select embodiments, the (co)polymer comprises poly(meth)acrylate (e.g., poly (methylmethacrylate) (PMMA)).

More particularly, suitable (co)polymers include polyolefins (e.g., polyethylene (such as low density polyethylene (LDPE), medium density polyethylene (MDPE), high density polyethylene (HDPE), and ultra high molecular weight polyethylene (UHMWPE)), polypropylene, polybutylene, ethylene co(co)polymers (e.g., polyethylene terephthalate (PET)), propylene co(co)polymers, butylene co(co)polymers, and co(co)polymers and blends of these (co)polymers). When polypropylene is used, the polypropylene may include alpha and/or beta phase polypropylene. PET includes carboxylate subunits formed from terephthalic acid or esters thereof and glycol subunits formed using ethylene glycol. Polycarbonate is a generic term used to describe polyester (co)polymers containing carbonate groups, and may be produced by the reaction of phosgene with bisphenol A.

Polyurethane is a generic term used to describe (co) polymers prepared by the reaction of a polyfunctional isocyanate with a polyfunctional alcohol to form urethane linkages. The term "polyurethane" has also been used more generically to refer to the reaction products of polyisocyanates with any polyactive hydrogen compound including polyfunctional alcohols, amines, and mercaptans. Polyurethane (co)polymers can be dispersed in water by incorporating stabilizing groups into their backbone. Anionic, cationic, and non-ionic dispersion stabilizing groups have been used. Various aqueous polyurethane dispersions have been prepared by those skilled in the art (e.g., U.S. Pat. No. 3,479,310 (Dieterich et al.) and U.S. Pat. No. 4,307,219 (Larson)). Examples of commercially available polyurethane emulsions include those aqueous aliphatic polyurethane emulsions available as NeoRez R-620, NeoRez R-961 and NeoRez R-966 from DSM. Suitable commercially available (co)polymeric dispersions include for example, an aliphatic polycarbonate/polyurethane dispersion, an aqueous anionic dispersion of an aliphatic polycarbonate polyurethane, a UV-curable polyurethane/acrylic co(co)polymer dispersion, and a UV-curable polyurethane dispersion, each of which is available from Alberdingk Boley (Greensboro, N.C.).

Suitable fluoro(co)polymers include a thermoplastic fluoro(co)polymer obtained by (co)polymerizing one or more types of fluorinated or partially fluorinated monomers. In this case, the specific microstructure of the fluoro(co)polymer allows for a certain degree of crystallinity of the fluoro(co)polymer, giving the thermoplastic properties. Generally, the thermoplastic fluoro(co)polymer is at least a co(co)polymer, but may be a ter(co)polymer or a thermoplastic fluoro(co)polymer that contains even four or more different co(co)polymerizable monomers. Co(co)polymerization allows for the decrease in crystallinity compared to the fluorine-based homopolymer, which can be advantageously used in the pressure-sensitive adhesive composition of this disclosure. Cross-linking of the thermoplastic fluoro (co)polymer can be performed generally with a peroxide, a polyol or a polyamine, but is not limited thereto. The fluoro(co)polymer may be a mixture of chemically different thermoplastic fluoro(co)polymers, as well as, mixtures of chemically different fluoroelastomers and mixtures of thermoplastic fluoro(co)polymers and fluoroelastomers.

For instance, suitable thermoplastic fluoro(co)polymers include co(co)polymers of tetrafluoroethene (TFE) with perfluorinated, partially fluorinated or non-fluorinated comonomers, wherein the comonomer content is 1 wt. % of greater, 3 wt. % or greater, and may be up to 30 wt. % (as used hereinabove and below the weight percentages are based on total weight of the (co)polymer—unless specified otherwise). Examples include: fluorinated ethylene propylene (FEP) (e.g., co(co)polymers of TFE, hexafluoropropylene (HFP), and other optional amounts of perfluorinated vinyl ethers); THV (e.g., co(co)polymers of TFE, vinylidine fluoride (VDF) and HFP), perfluoro alkoxy (PFA) (e.g., co(co)polymers of TFE and perfluoro alkyl vinyl ethers and/or perfluoro alkyl allyl ethers); homonomers and co(co)

polymers of VDF (e.g., PVDF); and homo- and co(co)polymers of chlortrifluoroethylene (CTFE) and co(co)polymers of TFE and ethylene (e.g., ETFE). Thermoplastic fluoro(co)polymers (sometimes referred to as fluorothermoplasts or fluorothermoplastics) are described, for example, in "Fluoro(co)polymer, Organic" in Ullmann's Encyclopedia of industrial chemisty, 7th edition, 2013, Wiley-VCH Verlag Chemie, Weinheim, Germany. Preferred fluorothermoplastics include fluoro(co)polymers with a melting point between 260 and 315° C., preferably 280° C. to 315° C.

As used herein, the term "polyester" refers to polyesters made from a single dicarboxylate monomer and a single diol monomer and also to copolyesters which are made from more than one dicarboxylate monomer and/or more than one diol monomer. In general, polyesters are prepared by condensation of the carboxylate groups of the dicarboxylate monomer with hydroxyl groups of the diol monomer. As used herein, the terms "dicarboxylate" and "dicarboxylic acid" are used interchangeably and include lower alkyl esters having from 1 to 10 carbon atoms. As used herein, diol monomers include those monomers having two or more hydroxyl groups, for example, diols, triols, tetraols, and pentaols. In general, useful sulfonated polyesters include those that are water soluble and those that are water dispersible. Molecular weights of from about 8000 to about 50000 may be useful. Amorphous sulfopolyesters described in U.S. Pat. No. 4,480,085 (Larson) may be useful. Sulfopolyesters described in U.S. Pat. No. 5,427,835 (Morrison et al.) may also be useful.

The sulfopolyester comprises at least one dicarboxylate monomer having one or more pendant sulfonate groups. Pendant sulfonate groups are groups that do not participate in (co)polymerization reactions that form the main backbone of polyesters. Examples of sulfonated dicarboxylate monomers include sulfonated derivatives of naphthalenedicarboxylic acid; terephthalic acid; phthalic acid; isophthalic acid; maleic acid; itaconic acid; azelaic acid; adipic acid; sebacic acid; succinic acid; glutamic acid; norbornenedicarboxylic acid; bicyclooctanedicarboxylic acid; 1,6-cyclohexanedicarboxylic acid; t-butylisophthalic acid; tri-mellitic acid; 4,4'-biphenyldicarboxylic acid; anthracenedicarboxylic acid; and tetradecanedicarboxylic acid.

Any of the sulfonated dicarboxylate monomers can be substituted by groups having a molecular weight of less than about 80 and which are inert in the (co)polymerization reaction. Examples of inert pendent groups include halogens, cyano, nitro, lower alkyl and alkoxy groups having from 1 to 4 carbon atoms, and phenyl groups. Additional dicarboxylate monomers are described in Larson. The pendant sulfonate groups may be introduced by grafting them onto side chains of a polyester, capping as end groups of a polyester, or including monomers having pendant sulfonated groups during (co)polymerization to form the polyester. Useful sulfopolyesters typically comprise at least two dicarboxylate monomers: one that is sulfonated as described above and one that is not. Unsulfonated dicarboxylate monomers that can be used include any of those described above for sulfonated derivatives.

Suitable poly(meth)acrylate (co)polymers preferably include zwitterionic co(co)polymers or cationic co(co)polymers. The zwitterionic co(co)polymers include the (co)polymerized product of an anionic monomer that is acrylic acid, methacrylic acid, a salt thereof, or a blend thereof; an acrylate or methacrylate ester of an alcohol having between 8 and 12 carbons; and a cationic monomer that is an acrylate or methacrylate ester having alkylammonium functionality. Optionally, one or more additional monomers are included in the zwitterionic co(co)polymers. In some embodiments the anionic monomer is acrylic or methacrylic acid, the acid is converted either before or after (co)polymerization to a corresponding carboxylate salt by neutralization. The cationic co(co)polymers include the (co)polymerized product of (co)polymerizable monomers including at least an acrylate or methacrylate ester of an alcohol having between 8 and 12 carbons and a cationic monomer that is an acrylate or methacrylate ester having an alkylammonium functionality. Optionally, one or more additional monomers are included in the cationic (co)polymers of the invention. In some embodiments, the acrylate or methacrylate ester is a mixture of two or more such esters; in some embodiments, the cationic monomer is a mixture of two or more such cationic monomers.

The acrylate or methacrylate ester of an alcohol having between 8 and 12 carbons may include acrylate or methacrylate esters of linear, branched, or cyclic alcohols (e.g., octyl, isooctyl, nonyl, isononyl, decyl, undecyl, and dodecyl alcohol). The (co)polymerized product of the acrylate or methacrylate ester of an alcohol having between 8 and 12 carbons is present in the cationic (co)polymer at about 50 wt % to 95 wt % of the total weight of the (co)polymer, or at about 60 wt % to 90 wt % of the total weight of the (co)polymer, or at about 75 wt % to 85 wt % of the total weight of the (co)polymer.

Often, the cationic monomer is an acrylate or methacrylate ester including an alkylammonium functionality, such as a 2-(trialkyl ammonium) ethyl acrylate or a 2-(trialkylammonium)ethyl methacrylate. A suitable monomer includes for example dimethylaminoethyl acrylate methyl chloride quaternary, available under the trade designation AGEFLEX FA1Q80MC from BASF (Ludwigshafen, Germany). The anion associated with the ammonium functionality of the cationic monomer is not particularly limited. In some embodiments, the anion is a halide anion (such as chloride, bromide, fluoride, or iodide), $BF_4$, $N(SO_2CF_3)_2$, $O_3SCF_3$, or $O_3SC_4F_9$, methyl sulfate, and/or hydroxide.

The (co)polymerized product of one or more additional monomers may be included in the cationic (co)polymers. Such additional monomers are not particularly limited by structure, but exclude monomers having anionic functionality. Non-limiting examples of additional monomers are N-vinyl pyrrolidone, isobutyl(meth)acrylate, n-butyl(meth)acrylate, isopropyl(meth)acrylate, n-propyl(meth)acrylate, methyl(meth)acrylate, ethyl(meth)acrylate, vinyl acetate, hydroxyethyl(meth)acrylate, hydroxypropyl(meth)acrylate, octadecyl(meth)acrylate, stearyl(meth)acrylate, dimethyl acrylamide, N-(hydroxymethyl)-acrylamide, dimethylaminoethyl(meth)acrylate, methoxy polyethylene glycol(meth)acrylate, polydimethylsiloxane(meth)acrylate), KF 2001 (mercapto modified dimethylsiloxane), perfluorobutyl sulfonamido n-methyl ethyl acrylate, and hexafluoropropylene oxide oligomer amidol(meth)acrylate.

Similarly, in embodiments, the (co)polymerized product of one or more additional monomers is included in the zwitterionic (co)polymers of the invention. Such additional monomers are not particularly limited by structure and include, in some embodiments, anionic functional monomers. Non-limiting examples of additional monomers are isobutyl acrylate, isobutyl methacrylate, n-butyl acrylate, n-butyl methacrylate, isopropyl acrylate, isopropyl methacrylate, n-propyl acrylate, n-propyl methacrylate, methyl acrylate, methyl methacrylate, ethyl acrylate, ethyl methacrylate, vinyl acetate, N-vinyl pyrrolidone, hydroxyethyl acrylate, or hydroxyethyl methacrylate. In some embodiments, the additional monomer is a mixture of two or more of these monomers. In some such embodiments, the additional monomer is vinyl acetate, N-vinyl pyrrolidone, isobutyl acrylate, a mixture of vinyl acetate and N-vinyl pyrrolidone, a mixture of vinyl acetate and isobutyl acrylate, or a mixture of isobutyl acrylate and N-vinyl pyrrolidone.

In some embodiments, the additional monomer has two or more (co)polymerizable functionalities; such monomers are referred to as cross-linkers. Cross-linkers that are useful in forming the cationic or zwitterionic (co)polymers include, without limitation, diacrylates such as ethylene glycol diacrylate, hexanediol diacrylate, and tripropyleneglycol diacrylate; triacrylates such as glycerol triacrylate and trimethylolpropane triacrylate; and tetraacrylates such as erythritol tetraacrylate and pentaerythritol tetraacrylate; divinyl benzene and derivatives thereof, and the like. In some embodiments, the crosslinker is a photoactive crosslinker. Photoactive cross-linkers include, for example, benzaldehyde, acetaldehyde, anthraquinone, substituted anthraquinones, various benzophenone-type compounds and certain chromophore-substituted vinylhalomethyl-s-triazines, such as 2,4-bis(trichloromethyl)-6-p-methoxystyryl-s-triazine. The (co)polymer is included in the radiation curable composition in an amount of 1 to 50 wt. %, inclusive, based on the total weight of the radiation curable composition, such as 25 to 50 wt. %, inclusive. Typically, the (co)polymer is included in the radiation curable composition in an amount of 1 wt. % or more, 2 wt. % or more, 5 wt. % or more, 7 wt. % or more, 10 wt. % or more, 12 wt. % or more, 15 wt. % or more, 20 wt. % or more, or 25 wt % or more; and 50 wt. % or less, 45 wt. % or less, 40 wt. % or less, 35 wt. % or less, or 30 wt. % or less, based on the total weight of the radiation curable composition.

Optional Emulsifier(s)

In certain embodiments, an emulsion may form containing the radiation hardenable component and any optional components.

The emulsion is a water-in-oil or an oil-in-water emulsion. In some such embodiments, the emulsion is an oil-in-water emulsion, wherein the (co)polymer and/or radiation hardenable components are stabilized in a bulk water phase by employing one or more emulsifiers (e.g., surfactants). In various embodiments, the emulsifier is cationic, anionic, zwitterionic, or non-ionic in nature and the structure thereof is not otherwise particularly limited. In some embodiments, the emulsifier is a monomer and becomes incorporated within the (co)polymer molecules formed from the radiation hardenable component. In other embodiments, the emulsifier is present in the (co)polymerization reaction vessel but is not incorporated into the (co)polymer molecules as a result of the (co)polymerization reaction.

Non-limiting examples of anionic emulsifiers useful in forming oil-in-water emulsions include ammonium, sodium, lithium, or potassium salts of lauryl sulfonic acid, dioctyl sodium sulfosuccinic acid, ammonium, sodium, lithium, or potassium salts of perfluorobutanesulfonic acid, ammonium, sodium, lithium, or potassium salts of perfluorooctanesulfonic acid, ammonium, sodium, lithium, or potassium salts of perfluorooctanoic acid, sodium dodecyl sulfate, sodium dodecylbenzenesulfonate, sodium laureth sulfate, sodium lauroyl sarcosinate, sodium myreth sulfate, sodium pareth sulfate, ammonium, sodium, lithium, or potassium salts of stearic acid, and combinations of one or more thereof.

Non-limiting examples of non-ionic emulsifiers useful in forming oil-in-water emulsions include block co(co)polymers of ethylene oxide and propylene oxide, such as those sold under the trade names PLURONIC, KOLLIPHOR, or TETRONIC, by the BASF Corporation of Charlotte, N.C.; ethoxylates formed by the reaction of ethylene oxide with a fatty alcohol, nonylphenol, dodecyl alcohol, and the like, including those sold under the trade name TRITON, by the Dow Chemical Company of Midland, Mich.; oleyl alcohol; sorbitan esters; alkylpolyglycosides such as decyl glucoside; sorbitan tristearate; and combinations of one or more thereof. In select embodiments, a suitable emulsifier comprises one or more non-ionic emulsifiers selected from ethoxylated alcohols, ethoxylated amines, amine oxides, and combinations thereof.

Non-limiting examples of cationic emulsifiers useful in forming oil-in-water emulsions include benzalkonium chloride, cetrimonium bromide, demethyldioctadecylammonium chloride, lauryl methyl gluceth-10 hydroxypropyl diammonium chloride, tetramethylammonium hydroxide, monoalkyltrimethylammonium chlorides, monoalkyldimethylbenzylammonium chlorides, dialkylethylmethylammonium ethosulfates, trialkylmethylammonium chlorides, polyoxyethylenemonoalkylmethylammonium chlorides, and diquaternaryammonium chlorides; the ammonium functional emulsifiers sold by Akzo Nobel N.V. of Amsterdam, the Netherlands, under the trade names ETHOQUAD, ARQUAD, and DUOQUAD; and mixtures thereof. Of particular use in forming oil-in-water emulsions are the ETHOQUAD surfactants, for example, ETHOQUAD C/12, C/25, C/12-75, and the like.

Where a cationic emulsifier is employed in an oil-in-water emulsion (co)polymerization reaction, it is employed in an amount of about 1.0 wt. % to 6.0 wt. % based on the total weight of the monomers, or at about 2.0 wt. % to 4.0 wt. % of the monomers, or in various intermediate levels such as 1.1 wt. %, 1.2 wt. %, 1.3 wt. %, 1.4 wt. %, 1.5 wt. %, 1.6 wt. %, 1.7 wt. %, 1.8 wt. %, 1.9 wt. %, 2.1 wt. %, 2.2 wt. %, and all other such individual values represented by 0.1 wt. % increments between 1.0 and 6.0 wt. %, and in any range spanning these individual values in 0.1 wt. % increments, such as 2.3 wt. % to 4.6 wt. %, 4.5 wt. % to 4.7 w.t %, and the like.

Optional Sensitizer(s)

In addition, a radiation curable composition as described herein can further comprise one or more sensitizers to increase the effectiveness of one or more photo-initiators that may also be present. In some embodiments, a sensitizer comprises isopropylthioxanthone (ITX) or 2-chlorothioxanthone (CTX). Other sensitizers may also be used. If used in the radiation curable composition, a sensitizer can be present in an amount ranging of about 0.01% by weight or about 1% by weight, based on the total weight of the radiation curable composition.

Optional(Co)Polymerization Inhibitor(s)

A radiation curable composition described herein optionally also comprises one or more (co)polymerization inhibitors or stabilizing agents. A (co)polymerization inhibitor is often included in a radiation curable composition to provide additional thermal stability to the composition. A stabilizing agent, in some instances, comprises one or more anti-oxidants. Any anti-oxidant not inconsistent with the objectives of the present disclosure may be used. In some embodiments, for example, suitable anti-oxidants include various aryl compounds, including butylated hydroxytoluene (BHT), which can also be used as a (co)polymerization inhibitor in embodiments described herein. In addition to or as an alternative, a (co)polymerization inhibitor comprises methoxyhydroquinone (MEHQ).

In some embodiments, a (co)polymerization inhibitor, if used, is present in an amount of about 0.001-2% by weight, 0.001 to 1% by weight, or 0.01-1% by weight, based on the total weight of the radiation curable composition. Further, if used, a stabilizing agent is present in a radiation curable composition described herein in an amount of about 0.1-5% by weight, about 0.5-4% by weight, or about 1-3% by weight, based on the total weight of the radiation curable composition.

Optional Absorption Modifier(s)

A radiation curable composition as described herein can also comprise one or more absorption modifiers (e.g., dyes, optical brighteners, pigments, particulate fillers, etc.) to control the penetration depth of actinic radiation. One particularly suitable absorption modifier is Tinopal OB, a benzoxazole, 2,2'-(2,5-thiophenediyl)bis[5-(1,1-dimethylethyl)], available from BASF Corporation, Florham Park, N.J. The absorption modifier, if used, can be present in an amount of about 0.001-5% by weight, about 0.01-1% by weight, about 0.1-3% by weight, or about 0.1-1% by weight, based on the total weight of the radiation curable composition.

Optional Colorant(s)

A radiation curable composition as described herein can also comprise one or more colorants such as dyes, pigments, and pigment dyes. Suitable colorants are described in U.S. Pat. No. 5,981,621 (Clark et al.), and include, for example, 1-hydroxy-4-[4-methylphenylamino]-9,10-anthracenedione (FD&C violet No. 2); disodium salt of 6-hydroxy-5-[(4-sulfophenyl)oxo]-2-naphthalenesulfonic acid (FD&C Yellow No. 6); 9-(o-carboxyphenyl)-6-hydroxy-2,4,5,7-tetraiodo-3H-xanthen-3-one, disodium salt, monohydrate (FD&C Red No. 3); and the like.

Examples of useful pigments include, without limitation: white pigments, such as titanium oxide, zinc phosphate, zinc sulfide, zinc oxide and lithopone; red and red-orange pigments, such as iron oxide (maroon, red, light red), iron/chrome oxide, cadmium sulfoselenide and cadmium mercury (maroon, red, orange); ultramarine (blue, pink and violet), chrome-tin (pink) manganese (violet), cobalt (violet); orange, yellow and buff pigments such as barium titanate, cadmium sulfide (yellow), chrome (orange, yellow), molybdate (orange), zinc chromate (yellow), nickel titanate (yellow), iron oxide (yellow), nickel tungsten titanium, zinc ferrite and chrome titanate; brown pigments such as iron oxide (buff, brown), manganese/antimony/titanium oxide, manganese titanate, natural siennas (umbers), titanium tungsten manganese; blue-green pigments, such as chrome aluminate (blue), chrome cobolt-alumina (turquoise), iron blue (blue), manganese (blue), chrome and chrome oxide (green) and titanium green; as well as black pigments, such as iron oxide black and carbon black. Combinations of pigments are generally used to achieve the desired color tone in the cured composition.

The use of fluorescent dyes and pigments can also be beneficial in enabling the printed composition to be viewed under black-light. A particularly useful hydrocarbon soluble fluorescing dye is 2,5-bis(5-tert-butyl-2-benzoxazolyl) 1 thiophene. Fluorescing dyes, such as rhodamine, may also be bound to cationic (co)polymers and incorporated as part of the resin.

Optional Fibrous Reinforcement Material(s)

A radiation curable composition as described herein can also comprise one or more fibrous reinforcement and Examples of suitable fibrous reinforcement include PGA microfibrils, collagen microfibrils, and others as described in U.S. Pat. No. 6,183,593 (Narang et al.). Discontinuous fibers are also suitable fillers, such as fibers comprising carbon, ceramic, glass, or combinations thereof. Suitable discontinuous fibers can have a variety of compositions, such as ceramic fibers.

The ceramic fibers can be produced in continuous lengths, which are chopped or sheared to provide the discontinuous ceramic fibers. The ceramic fibers can be produced from a variety of commercially available ceramic filaments.

Examples of filaments useful in forming the ceramic fibers include the ceramic oxide fibers sold under the trademark NEXTEL (3M Company, St. Paul, Minn.). NEXTEL is a continuous filament ceramic oxide fiber having low elongation and shrinkage at operating temperatures, and offers good chemical resistance, low thermal conductivity, thermal shock resistance, and low porosity. Specific examples of NEXTEL fibers include NEXTEL 312, NEXTEL 440, NEXTEL 550, NEXTEL 610 and NEXTEL 720. NEXTEL 312 and NEXTEL 440 are refractory aluminoborosilicate that includes $Al_2O_3$, $SiO_2$ and $B_2O_3$. NEXTEL 550 and NEXTEL 720 are aluminosilica and NEXTEL 610 is alumina.

During manufacture, the NEXTEL filaments are often coated with organic sizings or finishes which serves as aids in textile processing. Sizing can include the use of starch, oil, wax or other organic ingredients applied to the filament strand to protect and aid handling. The sizing can be removed from the ceramic filaments by heat cleaning the filaments or ceramic fibers as a temperature of 700° C. for one to four hours.

The ceramic fibers can be cut, milled, or chopped so as to provide relatively uniform lengths, which can be accomplished by cutting continuous filaments of the ceramic material in a mechanical shearing operation or laser cutting operation, among other cutting operations. Given the highly-controlled nature of certain cutting operations, the size distribution of the ceramic fibers is very narrow and allow to control the composite property. The length of the ceramic fiber can be determined, for instance, using an optical microscope (Olympus MX61, Tokyo, Japan) fit with a CCD Camera (Olympus DP72, Tokyo, Japan) and analytic software (Olympus Stream Essentials, Tokyo, Japan). Samples may be prepared by spreading representative samplings of the ceramic fiber on a glass slide and measuring the lengths of at least 200 ceramic fibers at 10× magnification.

Suitable fibers include for instance ceramic fibers available under the trade name NEXTEL (available from 3M Company, St. Paul, Minn.), such as NEXTEL 312, 440, 610 and 720. One presently preferred ceramic fiber comprises polycrystalline α-$Al_2O_3$. Suitable alumina fibers are described, for example, in U.S. Pat. No. 4,954,462 (Wood et al.) and U.S. Pat. No. 5,185,299 (Wood et al.). Exemplary alpha alumina fibers are marketed under the trade designation NEXTEL 610 (3M Company, St. Paul, Minn.). In some embodiments, the alumina fibers are polycrystalline alpha alumina fibers and comprise, on a theoretical oxide basis, greater than 99 percent by weight $Al_2O_3$ and 0.2-0.5 percent by weight $SiO_2$, based on the total weight of the alumina fibers. In other embodiments, some desirable polycrystalline, alpha alumina fibers comprise alpha alumina having an average grain size of less than one micrometer (or even, in some embodiments, less than 0.5 micrometer).

In some embodiments, polycrystalline, alpha alumina fibers have an average tensile strength of at least 1.6 GPa (in some embodiments, at least 2.1 GPa, or even, at least 2.8 GPa). Suitable aluminosilicate fibers are described, for example, in U.S. Pat. No. 4,047,965 (Karst et al). Exemplary aluminosilicate fibers are marketed under the trade designations NEXTEL 440, and NEXTEL 720, by 3M Company (St. Paul, Minn.). Aluminoborosilicate fibers are described, for example, in U.S. Pat. No. 3,795,524 (Sowman). Exemplary aluminoborosilicate fibers are marketed under the trade designation NEXTEL 312 by 3M Company. Boron nitride fibers can be made, for example, as described in U.S. Pat. No. 3,429,722 (Economy) and U.S. Pat. No. 5,780,154 (Okano et al.).

Ceramic fibers can also be formed from other suitable ceramic oxide filaments. Examples of such ceramic oxide filaments include those available from Central Glass Fiber Co., Ltd. (e.g., EFH75-01, EFH150-31). Also preferred are aluminoborosilicate glass fibers, which contain less than about 2% alkali or are substantially free of alkali (i.e., "E-glass" fibers). E-glass fibers are available from numerous commercial suppliers.

Optional Additive(s)

If desired, the compositions of the disclosure may contain other additives such as indicators, accelerators, surfactants, wetting agents, antioxidants, tartaric acid, chelating agents, buffering agents, and other similar ingredients that will be apparent to those skilled in the art. Additionally, medicaments or other therapeutic substances can be optionally added to the printed compositions. Examples include, but are not limited to, fluoride sources, whitening agents, anti-caries agents (e.g., xylitol), remineralizing agents (e.g., calcium phosphate compounds and other calcium sources and phosphate sources), enzymes, breath fresheners, anesthetics, clotting agents, acid neutralizers, chemotherapeutic agents, immune response modifiers, thixotropes, polyols, anti-inflammatory agents, antimicrobial agents, antifungal agents, agents for treating xerostomia, desensitizers, and the like, of the type often used in dental compositions.

Combinations of any of the above additives may also be employed. The selection and amount of any one such additive can be selected by one of skill in the art to accomplish the desired result without undue experimentation.

Additive Manufacturing Methods

The present disclosure also describes additive manufacturing processes useful in processing a radiation curable composition into near net shape (co)polymer-ceramic composite dental restorations. Thus in a further illustrative embodiment, the disclosure describes a method for producing a composite article, the method including the steps of (a) providing a radiation curable composition including at least one radiation curable (e.g., radiation hardenable) component, a photo-initiator, and a filler material having a population of particulates in an amount greater than or equal to 50% by weight of the printable composition, wherein the population of particulates exhibits a median diameter (D50) of greater than 0.3 micrometer on a volume-average basis as determined using the Particle Size Test Method, further wherein the radiation curable composition exhibits a viscosity of less than 150 Pa·s when measured using the Viscosity Test Method, optionally wherein the radiation curable composition is substantially free of organic solvents; and (b) selectively exposing a portion of the radiation curable composition to a source of actinic radiation to at least partially cure the exposed portion of the radiation curable composition, thereby forming a hardened layer, wherein steps (a) and (b) are repeated to form a near net-shape composite article.

In certain embodiments, the additive manufacturing process includes at least one of heating the radiation curable composition, removing uncured radiation curable composition from the near net-shape composite article, washing the near net-shape composite article with a solvent, or heating the near net-shape composite article.

The composite articles may include composite dental restorations, for example, dental crowns, bridges, inlays, onlays, veneers, pontics, or a combination thereof. In some embodiments, the composite article exhibits a Flexural Strength according to the Flexural Strength Test defined herein, of at least 80 MPa, at least 90 MPa, at least 100 MPa, at least 110 MPa, or even at least 120 MPS. In certain such embodiments, the Flexural Strength according to the Flexural Strength Test defined herein is at most 200 MPa, 175 MPa, 160 MPa, 150 MPa, or even 140 MPa.

In another illustrative embodiment, the present disclosure describes a method for making a dental crown, the method including the steps of (a) receiving a design for a dental crown having a wall having a bottom edge, and an occlusal portion joined with the wall opposite the bottom edge, the wall and the occlusal portion forming an interior surface and an opposing exterior surface, wherein the wall and the occlusal portion both comprise an additively manufacturable material; and (b) making the dental crown using an additive manufacturing method. The additive manufacturing method includes the steps of (i) providing a radiation curable composition including at least one radiation curable (i.e., photocurable) component, a photo-initiator, and a filler material having a population of particulates in an amount greater than or equal to 50% by weight of the printable composition, wherein the population of particulates exhibits a median diameter (D50) of greater than 0.3 micrometer on a volume-average basis as determined using the Particle Size Test Method, further wherein the radiation curable composition exhibits a viscosity of less than 150 Pa·s when measured using the Viscosity Test Method; and (ii) selectively exposing a portion of the radiation curable composition to a source of actinic radiation to at least partially cure the exposed portion of the radiation curable composition, thereby forming a hardened layer. Steps (i) and (ii) are repeated to form the dental crown as a near net-shape composite article. Optionally the radiation curable composition is substantially free of organic solvents and/or polymerizable monomers.

Turning now to the drawings, FIG. 1 is a flow chart representing a method for making (co)polymer-ceramic composite dental restorations, such as a dental crown, using an additive manufacturing device.

Once prepared as set forth above, the radiation curable compositions of the present disclosure may be used in myriad additive manufacturing processes to create a variety of articles, including casting a film as noted above. A generalized method for creating three-dimensional articles is illustrated in FIG. 1. Each step in the method will be discussed in greater detail below. First, in Step 110 the desired radiation curable composition is provided and introduced into a reservoir, cartridge, or other suitable container for use by or in a 3D printer. The 3D printer selectively cures the printed composition according to a set of computerized design instructions in Step 120 to create a gelled article representing the desired article. Once the initial curing process in complete, the temporary solvent is removed from the cured article in Step 130 via heating, solvent extraction, or other methods for removing solvent known in the art. Following the solvent removal processes of Step 130, the gelled article is subjected to additional curing to (co)polymerize remaining uncured radiation hardenable components in the gelled article in Step 140.

Methods of printing a three-dimensional article or object described herein can include forming the article from a plurality of layers of a radiation curable composition described herein in a layer-by-layer manner. Further, the layers of a build material composition can be deposited according to an image of the three-dimensional article in a computer readable format. In some or all embodiments, the radiation curable composition is deposited according to preselected computer aided design (CAD) parameters.

Additionally, it is to be understood that additive manufacturing methods described herein can include so-called "stereo-photolithography" (also known as "vat (co)polymerization") additive manufacturing methods. Other techniques for three-dimensional article manufacturing are known, and may be suitably adapted to use in the applications described herein. More generally, three-dimensional fabrication techniques continue to become available. All such techniques may be adapted to use with radiation curable compositions described herein, provided they offer compatible fabrication viscosities and resolutions for the specified article properties. Fabrication may be performed using any of the fabrication technologies described herein, either alone or in various combinations, using data representing a three-dimensional object, which may be reformatted or otherwise adapted as necessary for a particular printing or other fabrication technology.

It is entirely possible to form a 3D article from a radiation curable composition described herein using stereo-photolithography (e.g., vat (co)polymerization). For example, in some cases, a method of printing a 3D article comprises retaining a radiation curable composition described herein in a fluid state in a container and selectively applying energy to the radiation curable composition in the container to solidify at least a portion of a fluid layer of the radiation curable composition, thereby forming a hardened layer that defines a cross-section of the 3D article.

Additionally, a method described herein can further comprise raising or lowering the hardened layer of radiation curable composition to provide a new or second fluid layer of unhardened radiation curable composition at the surface of the fluid in the container, followed by again selectively applying energy to the radiation curable composition in the container to solidify at least a portion of the new or second fluid layer of the radiation curable composition to form a second solidified layer that defines a second cross-section of the 3D article.

Further, the first and second cross-sections of the 3D article can be bonded or adhered to one another in the z-direction (or build direction corresponding to the direction of raising or lowering recited above) by the application of the energy for solidifying the radiation curable composition. Moreover, selectively applying energy to the radiation curable composition in the container can comprise applying actinic radiation, such as UV radiation, visible radiation, or e-beam radiation, having a sufficient energy to cure the radiation curable composition.

A method described herein can also comprise planarizing a new layer of fluid radiation curable composition provided by raising or lowering an elevator platform. Such planarization can be carried out, in some cases, by utilizing a wiper or roller or a recoater bead. Planarization corrects the thickness of one or more layers prior to curing the material by evening the dispensed material to remove excess material and create a uniformly smooth exposed or flat up-facing surface on the support platform of the printer.

It is further to be understood that the foregoing process can be repeated a selected number of times to provide the 3D article. For example, in some cases, this process can be repeated "n" number of times. Further, it is to be understood that one or more steps of a method described herein, such as a step of selectively applying energy to a layer of radiation curable composition, can be carried out according to an image of the 3D article in a computer-readable format. Suitable stereo-photolithography printers include the Viper Pro SPLA, available from 3D Systems, Rock Hill, S.C. and the Asiga Pico Plus39, available from Asiga USA, Anaheim Hills, Calif.

Thus, in yet another illustrative embodiment, the present disclosure describes a stereo-photolithography apparatus including a vat; a radiation curable composition within the vat, a movable stage at least partially submerged in the radiation curable composition within the vat, and a source of actinic radiation adapted to selectively expose a portion of the radiation curable composition to the source of actinic radiation to at least partially cure the exposed portion of the radiation curable composition, thereby forming a hardened layer. The radiation curable composition includes at least one radiation hardenable component, a photo-initiator, and a filler material having a population of particulates in an amount greater than or equal to 50% by weight of the printable composition, wherein the population of particulates exhibits a median diameter (D50) of greater than 0.3 micrometer on a volume-average basis as determined using the Particle Size Test Method, further wherein the radiation curable composition exhibits a viscosity of less than 150 Pa·s when measured using the Viscosity Test Method. Optionally the radiation curable composition is substantially free of organic solvents and/or polymerizable monomers.

Figure 2:
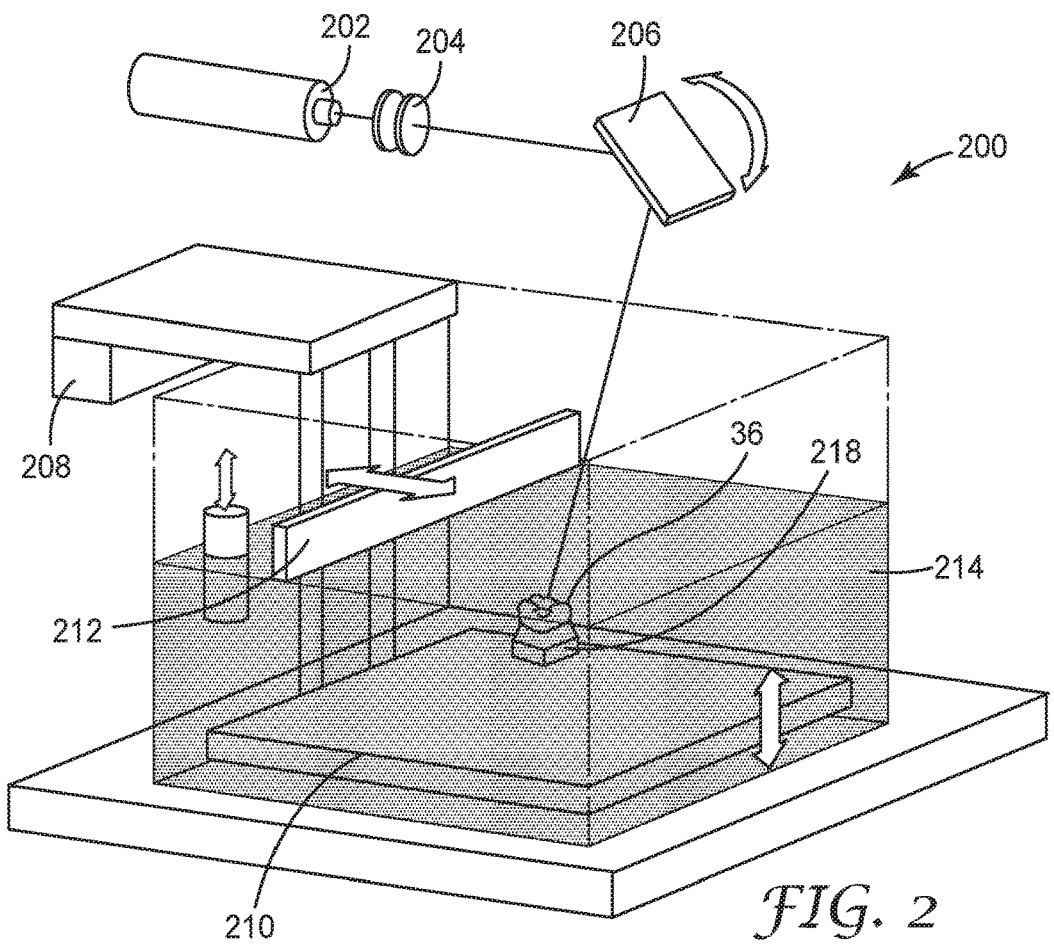
FIG. 2 is a diagram of an additive manufacturing device for making composite (co)polymer-ceramic dental restorations using stereo-photolithography according to the present disclosure.

FIG. 2 shows an exemplary stereo-photolithography apparatus ("SPLA") that may be used with the radiation curable compositions and methods described herein. In general, the SPLA 200 may include a laser 202, optics 204, a steering lens 206, an elevator 208, a platform 210, and a straight edge 212, within a vat 214 filled with the radiation curable composition. In operation, the laser 202 is steered across a surface of the radiation curable composition to cure a cross-section of the radiation curable composition, thereby forming a portion of a dental restoration 36, after which the elevator 208 slightly lowers the platform 210 and another cross section is cured. The straight edge 212 may sweep the surface of the cured composition between layers to smooth and normalize the surface prior to addition of a new layer. An optional scaffold or support 218 may, in some exemplary embodiments, be advantageously used to aid in forming the dental restoration 36.

In other embodiments, the vat 214 may be slowly filled with the radiation curable composition while a dental restoration is drawn, layer by layer, onto the top surface of the radiation curable composition.

A related technology, vat (co)polymerization with Digital Light Processing ("DLP"), also employs a container of curable (co)polymer (e.g., radiation curable composition). However, in a DLP based system, a two-dimensional cross section is projected onto the curable material to cure the desired section of an entire plane transverse to the projected beam at one time. In addition to the layer-by-layer stereolithography and DLP methods of vat polymerization, continuous printing in machines with these basic printer configurations is also possible, for example, by continuously advancing the build platform away from the surface of the polymerizing liquid such that additional liquid material is drawn into the build area during the polymerization process.

All such curable (co)polymer systems as may be adapted to use with the radiation curable compositions described herein are intended to fall within the scope of the term "stereo-photolithography system" as used herein.

More generally, the radiation curable composition is typically cured using actinic radiation, such as UV radiation, e-beam radiation, visible radiation, or any combination thereof. The skilled practitioner can select a suitable radiation source and range of wavelengths for a particular application without undue experimentation.

After the 3D article has been formed, it is typically removed from the stereo-photolithography additive manufacturing apparatus and rinsed, (e.g., an ultrasonic, or bubbling, or spray rinse in a solvent (which may be the same as or different from the temporary solvent in the radiation curable composition) which would dissolve a portion of the uncured radiation curable composition but not the cured, solid state gelled article (e.g., green body). Any other conventional method for cleaning the article and removing uncured material at the article surface may also be utilized. At this stage, the three-dimensional article typically has sufficient green strength for handling in the remaining steps of the method.

Referring once again to FIG. 1, the additively-manufactured green (co)polymer-ceramic composite restoration obtained in Step 120 will shrink (i.e., reduce in volume) such that the dimensions of the article after Step 130 will be smaller than expected. For example, a additively-manufactured (co)polymer-ceramic composite restoration may shrink about 6-8% in volume upon solvent removal, though this will not typically result in a significant distortion in the shape of the final object. It is particularly contemplated, therefore, that dimensions in the digital representation of the eventual cured article may be scaled according to a global scale factor to compensate for this shrinkage. For example, in some embodiments, at least a portion of the digital article representation can be at least 101% of the desired size of the printed appliance, in some embodiments at least 102%, in some embodiments at least 105%, in some embodiments, at least 110%, and in some embodiments, at least 120%.

A global scale factor may be calculated for any given radiation curable composition formulation by creating a calibration part according to Steps 110 and 120 above. The dimensions of the calibration article can be measured prior to the solvent removal of Step 130 and post-cure of Step 140.

In general, the three-dimensional article formed by the initial stereo-photolithography additive manufacturing step in Step 120, as discussed above, is not fully cured, by which is meant that not all of the (co)polymerizable material in the composition has (co)polymerized even after rinsing and solvent removal. Some uncured (co)polymerizable material is typically removed from the surface of the additively-manufactured (co)polymer-ceramic composite restoration during a cleaning process preceding the temporary solvent removal of Step 130. The article surface, as well as the bulk article itself, typically still retains uncured (co)polymerizable material, suggesting further cure. Removing residual uncured radiation curable composition is particularly useful when the gelled article is going to subsequently be post-cured, to minimize uncured residual radiation curable composition from undesirably curing directly onto the gelled article.

Further curing can be accomplished by further irradiating with actinic radiation, heating, or both. Exposure to actinic radiation can be accomplished with any convenient radiation source, generally UV radiation, visible radiation, and/or e-beam radiation, for a time ranging from about 10 to over 60 minutes. Heating is generally carried out at a temperature in the range of about 75-150° C., for a time ranging from about 10 to over 60 minutes in an inert atmosphere. So called post cure ovens, which combine UV radiation and thermal energy, are particularly well suited for use in the post cure process of Step 140. In general, postcuring improves the mechanical properties and stability of the three-dimensional article relative to the gelled article.

In select embodiments, the method optionally comprises heating the gelled article to within 10 degrees Celsius of the glass transition temperature ($T_g$) of the second (co)polymer for a time of at least 5 minutes. It has been unexpectedly discovered that such heating of the gelled article relaxes the (co)polymeric chains in the article to decrease internal strains without loss of the printed shape of the gelled article.

The optional post-processing step 140 can optionally include post-curing, support removal, extraction, and/or burn out, and then sintering and finishing of the additively-manufactured restoration.

Composite Dental Restorations

Figure 3:
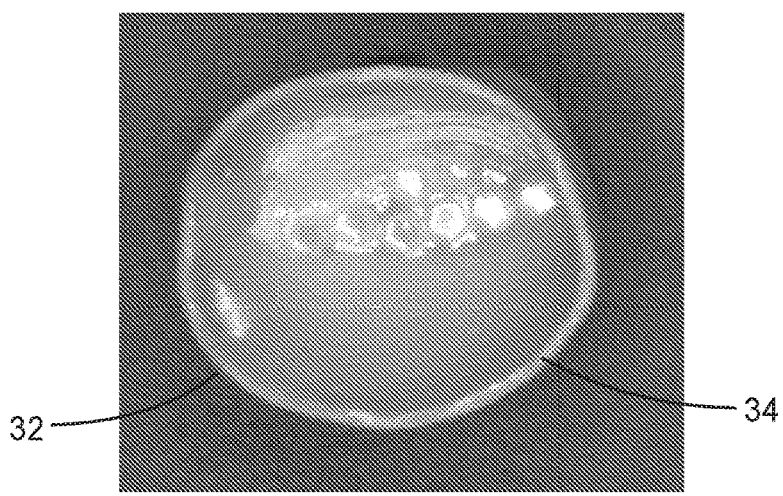
FIG. 3 is a first view of an image of a (co)polymer-ceramic composite dental crown made using an additive manufacturing process.
Figure 4:
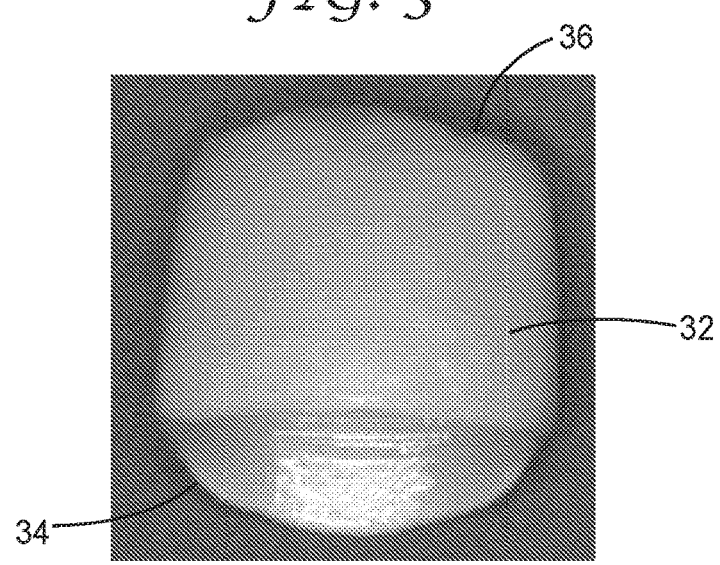
FIG. 4 is a second view of an image of a (co)polymer-ceramic composite dental crown made using an additive manufacturing process.
Figure 5:
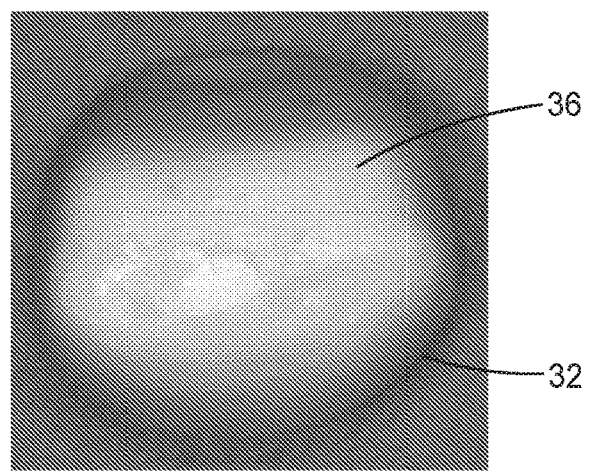
FIG. 5 is a third view of an image of a (co)polymer-ceramic composite dental crown made using an additive manufacturing process.

Various dental restorations (e.g., dental crowns as shown in FIGS. 3-5) may be produced using the exemplary radiation curable compositions and additive manufacturing methods described above.

As shown in FIGS. 3-5, additively-manufactured dental crowns generally have a wall 32 having a bottom edge 34 and an occlusal portion 36 joined with wall 32 opposite bottom edge 34. Wall 32 and occlusal portion 36 form an interior surface and opposing exterior surface.

The shape of the (co)polymer-ceramic composite restoration is not limited, and may comprise a film or a shaped integral (co)polymer-ceramic composite restoration. For instance, a film may readily be prepared by casting the radiation curable composition according to the first aspect, then subjecting the cast composition to actinic radiation to (co)polymerize the (co)polymerizable composition. In many embodiments, the (co)polymer-ceramic composite restoration comprises a shaped integral (co)polymer-ceramic composite restoration, in which more than one variation in dimension is provided by a single integral (co)polymer-ceramic composite restoration.

For example, the (co)polymer-ceramic composite restoration can comprise one or more channels, one or more undercuts, one or more perforations, or combinations thereof. Such features are not possible to provide in an integral (co)polymer-ceramic composite restoration using conventional molding methods.

An advantage of employing additive manufacturing processes such as stereo-photolithography or vat (co)polymerization is that a (co)polymer-ceramic composite restoration can be formed with a relatively low void content (e.g., empty spaces disposed within the (co)polymeric material). In some embodiments, the (co)polymer-ceramic composite restoration comprises a void content of ranging from 0.1 to 1.5%, inclusive, or ranging from 2.0 to 5.5%, inclusive. Such low void contents may provide benefits with respect to the flexural and/or tensile strength of the (co)polymer-ceramic composite restoration.

A radiation curable composition described herein in a cured state, in some embodiments, can exhibit one or more desired properties. A radiation curable composition in a "cured" state can comprise a radiation curable composition that includes a radiation hardenable component that has been at least partially (co)polymerized and/or crosslinked. For instance, in some instances, a cured (co)polymer-ceramic composite restoration is at least about 10% (co)polymerized or crosslinked or at least about 30% (co)polymerized or crosslinked. In some cases, a cured radiation curable composition is at least about 50%, at least about 70%, at least about 80%, or at least about 90% (co)polymerized or crosslinked. A cured radiation curable composition can also be between about 10% and about 99% (co)polymerized or crosslinked.

The conformability and durability of a substantially cured (co)polymer-ceramic composite restoration made from the radiation curable compositions of the present disclosure can be determined in part by standard flexural, tensile and elongation testing. The radiation curable compositions can typically be characterized by at least one of the following parameters after hardening. The elongation at break is typically 40% or greater, 50% or greater, 75% or greater, 100% or greater, 125% or greater, 150% or greater, or 200% or greater; and 600% or less, 500% or less, 400% or less, 300% or less, or 250% or less. Stated another way, the elongation at break of the cured (co)polymer-ceramic composite restoration can range from 40% to 600%. In some embodiments, the elongation at break is at least 50% and no greater than 500%.

The Flexural Strength of the substantially cured co)polymer-ceramic composite restoration made from the radiation curable compositions of the present disclosure as determined using the Flexural Strength Test Method hereinbelow, is typically at least 50 MPa, 75 MPa, 100 MPa, 125 MPa, or even 140 MPa. The Flexural Tensile Strength is typically at most 200 MPa, 175 MPa, 150 MPa, or even 140 MPa.

The mechanical properties above are particularly well suited for polymer-ceramic composite restorations that require resiliency and flexibility, along with adequate wear strength and low hygroscopicity.

System for Additive Manufacturing of Polymer-Ceramic Composite Dental Restorations In a further illustrative embodiment, the present disclosure describes a system including a display that displays a 3D model of a dental restoration, and one or more processors that, in response to the 3D model selected by a user, cause an additive manufacturing device to create a near net shape composite dental restoration using an additive manufacturing method. The additive manufacturing method includes the steps of (a) providing a radiation curable composition, and (b) selectively exposing a portion of the radiation curable composition to a source of actinic radiation to at least partially cure the exposed portion of the radiation curable composition, thereby forming a hardened layer. Steps (a) and (b) are repeated to form the near net-shape composite dental restoration. The radiation curable composition includes at least one radiation curable (e.g., radiation hardenable) component, a photo-initiator, and a filler material having a population of particulates in an amount greater than or equal to 50% by weight of the printable composition, wherein the population of particulates exhibits a median diameter (D50) of greater than 0.3 micrometer on a volume-average basis as determined using the Particle Size Test Method, further wherein the radiation curable composition exhibits a viscosity of less than 150 Pa·s when measured using the Viscosity Test Method.

The additive manufacturing system of the present disclosure makes use of an additive manufacturing device and process to produce three-dimensional (3D) (co)polymer-ceramic composite (co)polymer-ceramic composite restorations. One particularly-preferred additive manufacturing process is stereo-photolithography. In stereo-photolithography, the desired 3D (co)polymer-ceramic composite restoration is built up from a liquid photocurable composition with the aid of an alternating sequence of two steps, which may be repeated any number of times.

In the first step, a layer of the liquid photocurable composition, one boundary of which is the surface of the composition, is cured with the aid of appropriate radiation within a surface region which corresponds to the desired cross-sectional area of the shaped (co)polymer-ceramic composite restoration to be formed, at the height of this layer, and in the second step, the cured layer is covered with a new layer of the liquid, curable composition, and the sequence of steps is repeated until a so-called green body (i.e., gelled (co)polymer-ceramic composite restoration) of the desired shape is finished. This green body is, in general, not yet fully cured and must, normally, be subjected to post-curing. The mechanical strength of the green body immediately after curing, otherwise known as green strength, is relevant to further processing of the printed (co)polymer-ceramic composite restorations.

Figure 6:
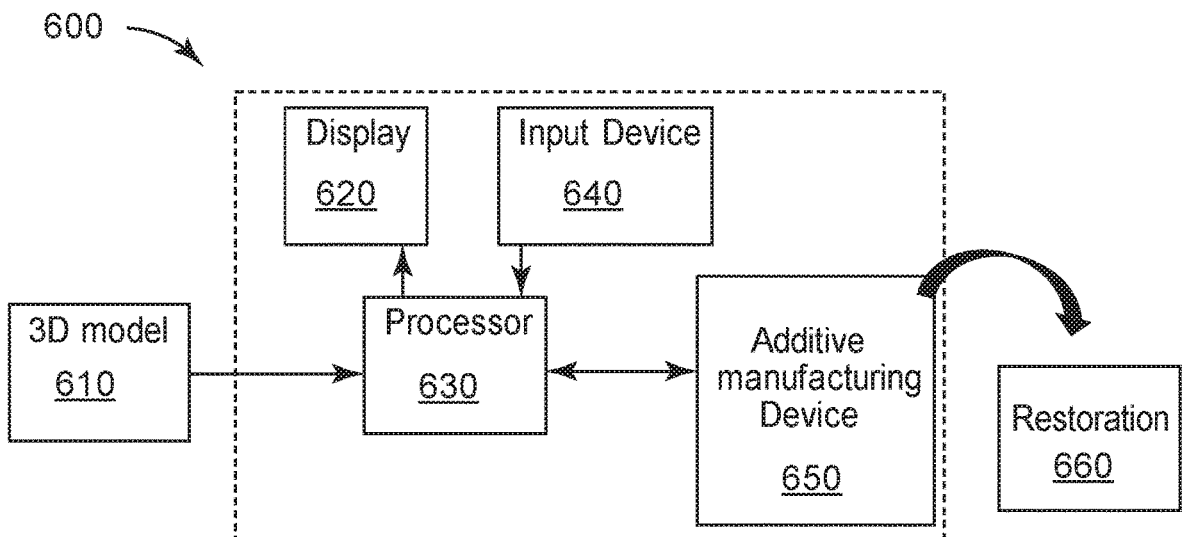
FIG. 6 is a block diagram of a generalized system for additive manufacturing of composite (co)polymer-ceramic dental restorations.
Figure 10:
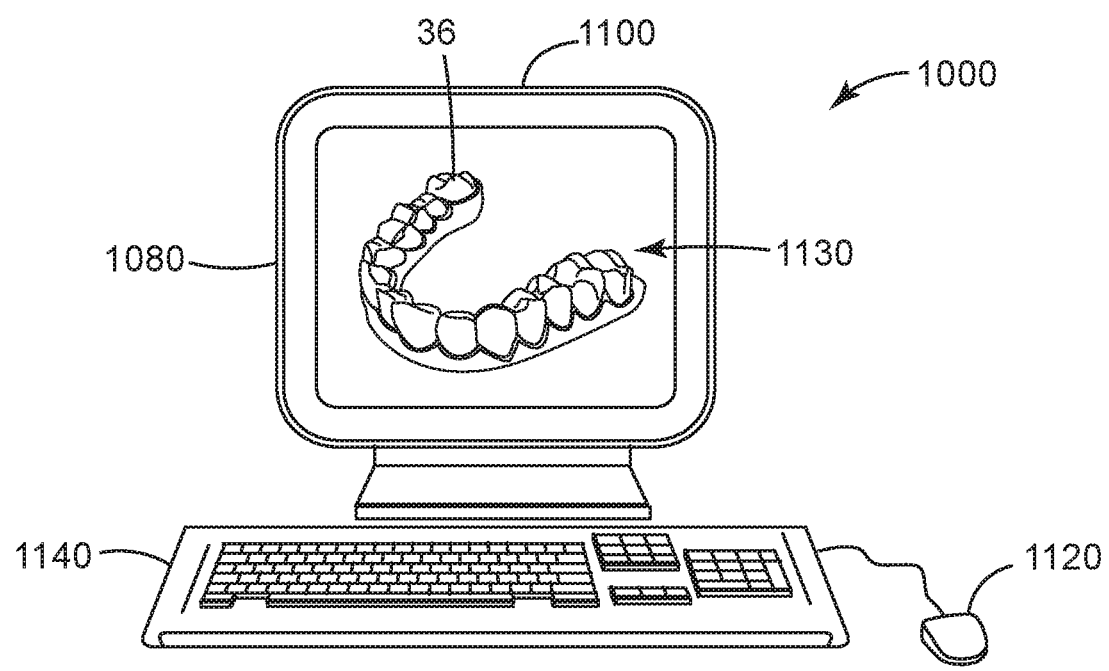
FIG. 10 is a schematic front view of an exemplary computing device useful in generating composite (co)polymer-ceramic dental restorations using an additive manufacturing process.

Referring now to FIG. 6, in certain embodiments, the present disclosure provides a system 600. The system 600 comprises a display 620 that displays a 3D model 610 of a dental restoration (e.g., a dental crown 36 corresponding to a position on a 3D representation of an individual's teeth 1130, as shown on the display of FIG. 10); and one or more processors 630 that, in response to the 3D model 610 selected by a user, cause an additive manufacturing device 650 to create a physical object of the restoration 660. Often, an input device 640 (e.g., keyboard and/or mouse) is employed with the display 620 and the at least one processor 630, particularly for the user to select the 3D model 610. The article 660 comprises an integral blend of 8 to 50 wt. %, inclusive, of a thermoset (co)polymer and 30 to 90 wt. %, inclusive, of a second (co)polymer different from the thermoset (co)polymer, wherein the weight percent is based on the total weight of the article.

Figure 7:
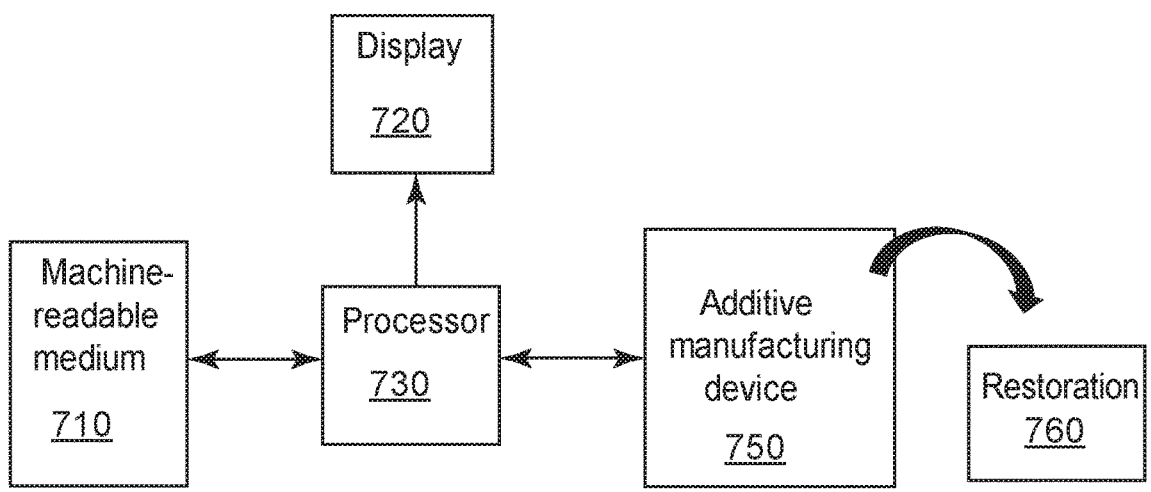
FIG. 7 is a block diagram of a generalized manufacturing process for composite (co)polymer-ceramic dental restorations.

Referring to FIG. 7, a processor 720 (or more than one processor) is in communication with each of a machine-readable medium 710 (e.g., a non-transitory medium), a 3D printer/additive manufacturing device 740, and optionally a display 730 for viewing by a user. The additive manufacturing device 740 is configured to make one or more dental restorations 750 based on instructions from the processor 720 providing data representing a 3D model of the composite restoration 760 (e.g., a dental crown 36 based on a 3D representation of an individual's teeth 1130, as shown on the display 1100 of FIG. 10) from the machine-readable medium 710.

Figure 8:
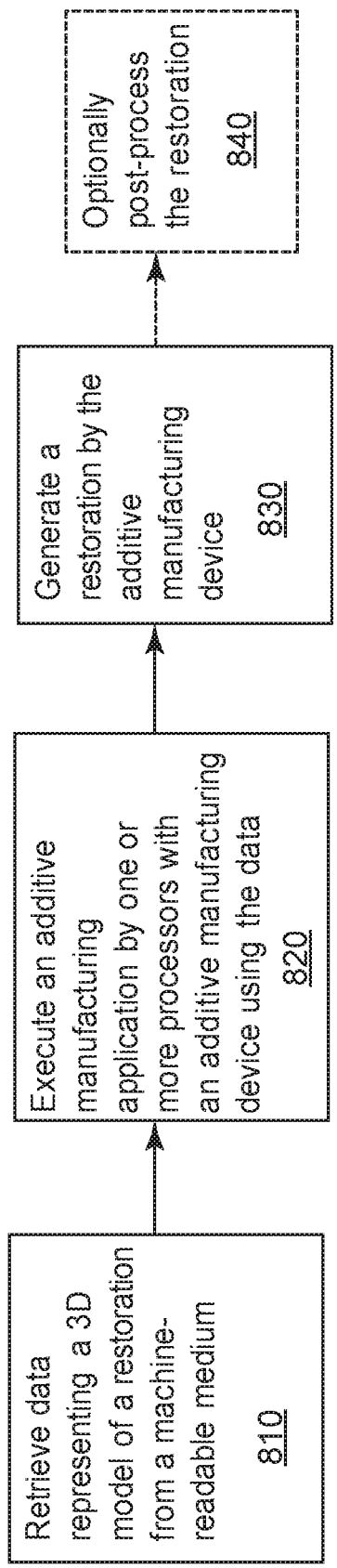
FIG. 8 is a high-level flow chart of an exemplary manufacturing process for composite (co)polymer-ceramic dental restorations.

Referring to FIG. 8, which illustrates, for example and without limitation, an additive manufacturing method comprises retrieving 810, from a (e.g., non-transitory) machine-readable medium, data representing a 3D model of a dental restoration according to at least one embodiment of the present disclosure. The method further includes executing 820, by one or more processors, an additive manufacturing application interfacing with a manufacturing device using the data; and generating 830, by the manufacturing device, a physical object of the article. The additive manufacturing equipment can selectively cure a radiation curable composition to form an at least partially cured or gelled restoration. One or more various optional post-processing steps 840 may be undertaken. Typically, next at least a portion of any optional temporary solvent is removed from the gelled article, and optionally, any unreacted radiation hardenable component remaining, either before or after removing any temporary solvent, may then be cured to form a substantially cured composite dental restoration.

Figure 9:
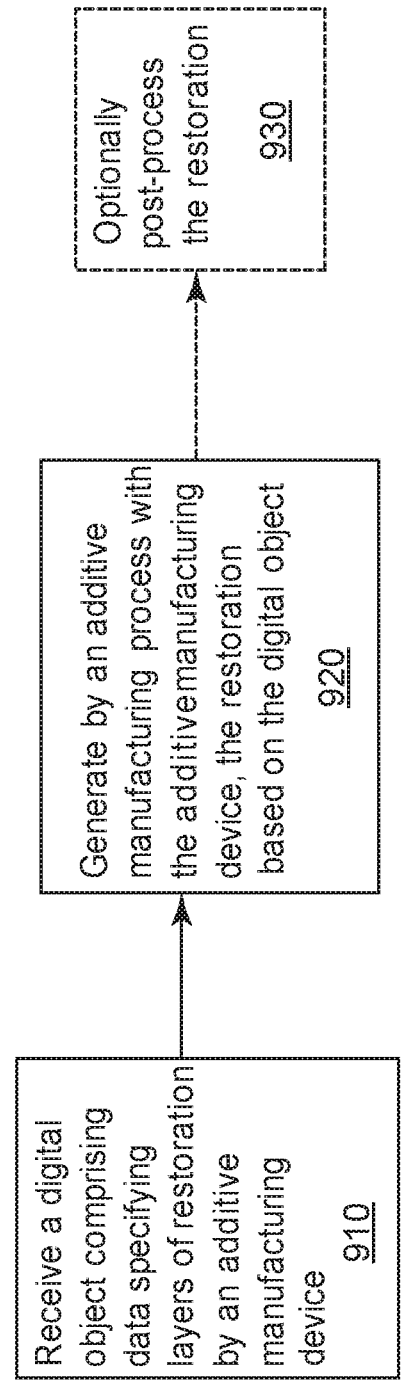
FIG. 9 is a high-level flow chart of an exemplary additive manufacturing process for composite (co)polymer-ceramic dental restorations.

Additionally, referring to FIG. 9, a method of making a dental restoration comprises receiving 910, by a manufacturing device having one or more processors, a digital object comprising data specifying a plurality of layers of a dental restoration; and generating 920, with the manufacturing device by an additive manufacturing process, the article based on the digital object. The composite dental restoration may undergo one or more optional steps of post-processing 930, for example, at least one of heating the radiation curable composition, removing uncured radiation curable composition from the near net-shape composite article, washing the near net-shape composite article with a solvent, or heating the near net-shape composite article.

In further exemplary embodiments, it may be desirable that the composite dental restoration be heated at a temperature to substantially fully cure the composite composition, or cause sintering of the plurality of particulates. Suitable temperatures may be at least about 90° C., 100° C., 110° C., 120° C., 125° C., or even 130° C.; but preferably no more than about 250° C., 225° C., 200° C., 175° C., or even 150° C.

The operation of the present disclosure will be further described with regard to the following detailed examples. These examples are offered to further illustrate the various specific and preferred embodiments and techniques. It should be understood, however, that many variations and modifications may be made while remaining within the scope of the present disclosure.

EXAMPLES

These Examples are merely for illustrative purposes and are not meant to be overly limiting on the scope of the appended claims. Notwithstanding that the numerical ranges and parameters setting forth the broad scope of the present disclosure are approximations, the numerical values set forth in the specific examples are reported as precisely as possible. Any numerical value, however, inherently contains certain errors necessarily resulting from the standard deviation found in their respective testing measurements. At the very least, and not as an attempt to limit the application of the doctrine of equivalents to the scope of the claims, each numerical parameter should at least be construed in light of the number of reported significant digits and by applying ordinary rounding techniques.

Summary of Materials

As used herein, all parts and percentages are by weight (wt. %), unless otherwise specified. All water is deionized water, and all molecular weights are average molecular weights, unless otherwise specified. Unless otherwise specified, materials can be obtained from Sigma-Aldrich, Milwaukee, Wis. Unless otherwise specified, all 3D printing examples employed an ASIGA PICO 2, a vat (co)polymerization 3D printer available from Asiga USA, Anaheim Hills, Calif.

TABLE 1A

Materials

| Material | Description | Source |
| --- | --- | --- |
| SR-348 | Ethoxylated (2) bisphenol A dimethacrylate | Sartomer (Exton, PA) |
| UDMA | Urethane dimethacrylate | Esstech Inc., (Essington, PA) |
| Procrylat | 2,2-Bis-4-(3-methacryloxypropoxy)phenyl)propane dimethacrylate, as further described in U.S. Pat. No. 8,389,599 | 3M Company (St. Paul, MN) |
| TEGDMA | Triethyleneglycol dimethacrylate | Sigma-Aldrich (St. Louis, MO) |
| DDDMA | 1,12-Dodecanediol dimethacrylate | Sartomer (Exton, PA) |
| BisGMA | Bisphenol A-glycidyl methacrylate | 3M Company |
| PGT-IEM | Inventive example 1 as described in WO2015126666A1 | 3M Company |
| IRGAGURE TPO | 2,4,6-Trimethylbenzoyldiphenylphosphine oxide (photo-initiator) | BASF (Wyandotte, MI) |
| BHT | 2,6-Di-tert-butyl-4-methyl-phenol (Butylated hydroxytoluene. BHT) | Fluka Analytical (St. Louis, MO) |
| TINOPAL OB | 2,5-Thiophenediylbis(5-tert-butyl-1,3-benzoxazole) (optical brightener) | BASF, Wyandotte, MI |
| 1-methoxy-2-propanol | 1-methoxy-2-propanol | Sigma-Aldrich |

TABLE 1B

Materials - Fillers

| Material | Description | Source |
| --- | --- | --- |
| S/T Silica/Zirconia Clusters | Silane-treated silica-zirconia nano-cluster filler, prepared generally as described in U.S. Pat. No. 6,730,156 at column 25, lines 50-63 (Preparatory Example A) and at column 25, line 64 through column 26, line 40 (Preparatory Example B) with minor modifications, including performing the silanization in 1-methoxy-2-propanol (rather than water) adjusted to a pH of ~8.8 with aqueous NH4OH (rather than to a pH of 3-3.3 with trifluoroacetic acid), and obtaining the nano-cluster filler by gap drying (rather than spray drying). | 3M Company |

TABLE 1B-continued

Materials - Fillers

| Material | Description | Source |
|---|---|---|
| S/T Zirconia/Silica | Zirconia-silica filler (which can be prepared as described in U.S. Pat. No. 6,624,211 at column 15, line 60 through column 16, line 28) silane-treated in the following manner. One hundred parts of the filler (average particle size 0.6-0.9 micrometers) was mixed with deionized water at a solution temperature of between 20-30° C., and the pH was adjusted to 3-3.3 with trifluoroacetic acid (0.278 parts). 3-Methacryloxypropyltrimethoxysilane (available from Wacker Chemie AG, Munich, Germany) was added to the slurry in an amount of 7 parts, and the blend was mixed for 2 hours. At the end of 2 hours, the pH was neutralized with calcium hydroxide. The filler was dried, crushed and screened through a 74 micron screen. | 3M Company |
| S/T 20 nm Silica | Silane-treated silica nanoparticle filler having a nominal particle size of approximately 20 nanometers, prepared generally as described in U.S. Pat. No. 6,572,693 at column 21, lines 63-67 (Nanosized particle filler, Type #2). | 3M Company |
| S/T 75 nm Silica | Silane-treated silica nanoparticle filler having a nominal particle size of approximately 75 nanometers, prepared generally as described in U.S. Pat. No. 6,899,948 at column 31, lines 30-40 (Filler C: Nano-sized Silica). | 3M Company |

Preparation of Unfilled Resins

Unfilled resins were prepared according to the formulations listed in Table 1, by roller mixing the components overnight to ensure thorough mixing.

TABLE 2

Unfilled Resin Formulations (wt. %)

| Unfilled Resin ID: | R1 | R2 | R3 | R4 |
|---|---|---|---|---|
| BisGMA | 49.41 | — | 14.82 | — |
| TEGDMA | 49.41 | — | 14.82 | — |
| UDMA | — | 34.59 | 34.59 | 16.2 |
| PROCRYLAT | — | 29.64 | — | — |
| SR-348 | — | 34.59 | 34.59 | — |
| PGT-IEM | — | — | — | 75.8 |
| DDDMA | — | — | — | 8 |
| IRGACURE TPO | 0.99 | 0.99 | 0.99 | — |
| TINOPAL OB | 0.099 | 0.099 | 0.099 | — |
| BHT | 0.099 | 0.099 | 0.099 | — |

Preparation of Filled Resins

Filled resins (i.e., printing compositions) were prepared according to the formulations listed in Table 3 by speed-mixing the resin and filler components in a Thinky planetary mixture at 2000 rpm for one minute. Mixing was repeated 4 times, while allowing the printing composition to cool to room temperature between mixing cycles.

TABLE 3

Filled Resin Formulations (amounts in grams)

| Filled Resin ID | Unfilled Resin ID | Unfilled Resin | S/T Silica/ Zirconia Clusters | S/T Zirconia/ Silica | S/T 20 nm Silica | S/T 75 nm Silica |
|---|---|---|---|---|---|---|
| F1 | R2 | 66.6 | 26.7 | — | 6.7 | — |
| F2 | R2 | 50 | 50 | — | — | — |
| F3 | R2 | 40 | 50 | — | — | 10 |
| F4 | R2 | 50 | — | 50 | — | — |
| F5 | R2 | 50 | — | 40 | — | 10 |
| F6 | R1 | 30 | — | 60 | — | 10 |
| F7 | R3 | 40 | 60 | — | — | — |
| F8* | R4 | 24 | 68.8 | — | — | 7.2 |

*same as Dental Composition B on page 76 of WO20156666A1

Test Methods

The following test methods have been used in evaluating some of the Examples of the present disclosure.

Particle Size Test Method

Particle size distribution of the filled resins were determined as follows. The filled resins were diluted in 1-methoxy-2-propanol 1:1000 by volume before introducing it into the recirculation pool. The particle size distributions were measured using laser diffraction particle size analysis on a Horiba particle size distribution analyzer, Model LA-950V2. The volume average D10, D50 (median), and D90 values (in micrometers, μm) for each filled resin are shown in Table 4.

TABLE 4

Volume Average Particle Size in Micrometers for the Filled Resins

| Filled Resin ID | D10 | D50 | D90 |
|---|---|---|---|
| F1 | 2.58 | 6.30 | 65.17 |
| F2 | 0.33 | 1.87 | 4.06 |
| F3 | 0.23 | 3.49 | 7.91 |
| F4 | 0.15 | 0.38 | 10.01 |
| F5 | 0.15 | 0.37 | 11.73 |
| F6 | 0.14 | 0.33 | 3.45 |
| F7 | 0.26 | 3.40 | 6.75 |

Viscosity Test Method

Absolute viscosities of the unfilled and filled resins were measured using a TA Instruments AR-G2 magnetic bearing rheometer using a 40 mm cone and plate measuring system at 40° C. at a shear rate of 0.1 sec$^{-1}$). Two replicates were measured and the average value was reported as the viscosity, in Pa·s.

TABLE 5

Viscosities of Unfilled and Filled Resins
in Pa · s, as a Function of Temperature

| Resin ID | Viscosity (Pa · S) at 40° C. |
|---|---|
| R1 | 0.09 |
| R2 | 0.44 |
| R3 | 0.38 |
| F1 | 1.15 |
| F2 | 1.39 |
| F3 | 86.98 |
| F4 | 27.15 |

TABLE 5-continued

Viscosities of Unfilled and Filled Resins
in Pa · s, as a Function of Temperature

| Resin ID | Viscosity (Pa · S) at 40° C. |
|---|---|
| F5 | 135.0 |
| F6 | 22.4 |
| F7 | 2.18 |
| F8 | 51,485.0 |

Sedimentation and Phase Separation Stability Test Method

The filled resins were kept in a clear glass vial at room temperature and were observed for settling/phase separation at room temperature. All filled resin examples F1-F7 were determined to be stable for at least one month at room temperature (~22° C.), in that no particle settling was detected. After 4 months, some sediment was detected at the bottom of the vial for F1, F2, F7. Settling was not detected for filled resin examples: F3, F4, F5, and F6.

Flexural Strength Test Method

Comparative Examples CE-1-CE-6 and Examples EX-1-EX-6

Unfilled and filled resins were printed on the Asiga Pico 2 printer with a LED light source of 385 nm and ~23 mW/cm$^2$ of power. Flexural test bars prepared according to ISO-4049 standard (2×2×25 mm) were printed with the 2×2 face on the build plate. The resin bath of the printer was heated to 35-40° C. before printing to reduce the viscosity to be able to print. The printing temperature of each formulation is listed in Table 5. The following settings were used: Slice thickness=50 µm, Burn-In Layers=3, Separation Velocity=10 mm/s, Slides per Layer=1, Burn-In Exposure Time=15.0 s, Normal Exposure Time=1.5 s. The printed bars were then washed with isopropyl alcohol to remove the excess uncured resin. The test bars were then post-cured under fusion lamps for 90 minutes on each side. The post-cured test bars were then tested in a 3-point bend fixture according to ISO-4049 standard. The flexural strength and modulus of post-cured test bars are reported in megapascals (MPa) and gigapascals (GPa), respectively.

TABLE 6

Flexural Strength (MPa) and Flexural Modulus (GPa) Data
and Printing Temperature for 3D-Printed Test Bars

| Example | Resin ID | Flexural Strength (Std. Dev.) | Flexural Modulus (Std. Dev.) | Printing Temperature (° C.) |
|---|---|---|---|---|
| CE-1** | FILTEK* | 141.02 (15.5) | 11.92 (0.9) | NA |
| CE-2 | R2 | 100.8 (1.7) | 2.28 (0.14) | Room Temp |
| CE-3 | R1 | 84 (25) | 2.34 (0.12) | Room Temp |
| CE-4 | R3 | 98.4 (4.0) | 2.45 (0.09) | Room Temp |
| CE-5 | F1 | 80.3 (11.3) | 3.41 (0.13) | 35 |
| CE-6** | F8 | Not printable | Not printable | Not printable |
| EX-1 | F2 | 122.9 (9.4) | 5.2 (0.17) | 40 |
| EX-2 | F3 | 108.5 (21.7) | 6.81 (0.30) | 40 |
| EX-3 | F4 | 102.9 (6.5) | 4.64 (0.17) | 35 |
| EX-4 | F5 | 126.1 (1.8) | 4.67 (0.25) | 35 |
| EX-5 | F6 | 113.1 (12.3) | 7.67 (0.41) | 35 |
| EX-6 | F7 | 87.5 (12.3) | 6.69 (0.11) | 35 |

*FILTEK Supreme Ultra Universal Restorative, available from 3M Oral Care, St. Paul MN.
**Samples were too high in viscosity to be printable using Vat (co)polymerization. CE-1 was cast in metal molds and cured using light to get the flexural bars.

3D Printing of Unfilled and Filled Resins

The above data suggests that higher loading of particles (>50 wt %) is needed to get good flexural strength and modulus that would be desirable for permanent restoratives, such as dental crowns. Comparative Example CE-5 which has low particle loading shows low strength and modulus, whereas EX-1 and EX-4, show strengths approaching ~125 MPa, close to CE-1, which is a commercially available product used for permanent restoratives. Though printed in a layer-by-layer fashion, EX-1-EX-6 show acceptable properties in the range needed for permanent dental restorations.

3D Printing of a Dental Crown

Example EX-7

A dental crown was 3D printed using filled resin F4 on the ASIGA PICO 2 printer employing the following settings: The following settings for printing were used: Slice thickness=50 µm, Burn-In Layers=2, Separation Velocity=10 mm/s, Slides per Layer=1, Burn-In Exposure Time=20.0 s, Normal Exposure Time=1.5, Vat temperature=35° C. To generate this crown a 3D scan (3M Lava Scan) was made of a commercially available pediatric crown (3M Stainless Steel) to generate a surface mesh file. This file was imported into Geomagic Studio where it was processed to yield a 300 micron thick shell. The STL file was exported and sent to post processing software (Asiga) where supports were added and slices were generated. After printing, the dental crown was removed from the build plate, rinsed with isopropyl alcohol, and post-cured in an ASIGA UV chamber for 90 minutes.

Reference throughout this specification to "one embodiment," "certain embodiments," "one or more embodiments" or "an embodiment," whether or not including the term "exemplary" preceding the term "embodiment," means that a particular feature, structure, material, or characteristic described in connection with the embodiment is included in at least one embodiment of the certain exemplary embodiments of the present disclosure. Thus, the appearances of the phrases such as "in one or more embodiments," "in certain embodiments," "in one embodiment" or "in an embodiment" in various places throughout this specification are not necessarily referring to the same embodiment of the certain exemplary embodiments of the present disclosure. Furthermore, the particular features, structures, materials, or characteristics may be combined in any suitable manner in one or more embodiments.

While the specification has described in detail certain exemplary embodiments, it will be appreciated that those skilled in the art, upon attaining an understanding of the foregoing, may readily conceive of alterations to, variations of, and equivalents to these embodiments. Accordingly, it should be understood that this disclosure is not to be unduly limited to the illustrative embodiments set forth hereinabove.

Furthermore, all publications and patents referenced herein are incorporated by reference in their entirety to the same extent as if each individual publication or patent was specifically and individually indicated to be incorporated by reference. Various exemplary embodiments have been described. These and other embodiments are within the scope of the following claims.

What is claimed is:

1. A radiation curable composition comprising:
   at least one radiation hardenable component;
   an optical brightener in an amount of 0.01-1% by weight, based on the total weight of the radiation curable composition;
   a photo-initiator; and
   a filler material comprising a population of particulates in an amount greater than or equal to 50% by weight of the printable composition, wherein the population of particulates comprises a nano-filler, wherein the nano-filler comprises nano-clusters, and wherein the population of particulates exhibits a median diameter (D50) of greater than 0.3 micrometer on a volume-average basis as determined using a Particle Size Test Method of the description, further wherein the radiation curable composition exhibits a viscosity of less than 150 Pa·s when measured using a Viscosity Test Method of the description.

2. The radiation curable composition of claim 1, wherein the at least one radiation hardenable component is ethylenically-unsaturated.

3. The radiation curable composition of claim 2, wherein the at least one radiation hardenable component is selected from the group consisting of dimers, trimers, oligomers, and combinations thereof.

4. The radiation curable composition of claim 1, wherein the photo-initiator is not a cationic photo-initiator.

5. The radiation curable composition of claim 4, wherein the photo-initiator is a photo-radical photo-initiator.

6. The radiation curable composition of claim 1, wherein the filler material comprises inorganic particulates.

7. The radiation curable composition of claim 6, wherein the inorganic particulates comprise a metal, a metal alloy, a metal oxide, a metal nitride, a metal carbide, carbon, and combinations thereof.

8. The radiation curable composition of claim 7, wherein the inorganic particulates are surface treated.

9. The radiation curable composition of claim 1, further comprising at least one additive selected from the group consisting of a solvent, a monomer, a (co)polymer, an emulsifier, a polymerization inhibitor, a photosensitizer, a colorant, a fiber reinforcement material, or a combination thereof.

10. A method for producing a composite article, the method comprising the steps of:
    (a) providing a radiation curable composition including:
       at least one radiation hardenable component;
       an optical brightener in an amount of 0.01-1% by weight, based on the total weight of the radiation curable composition;
       a photo-initiator; and
       a filler material comprising a population of particulates in an amount greater than or equal to 50% by weight of the printable composition, wherein the population of particulates comprises a nano-filler, wherein the nano-filler comprises nano-clusters, and wherein the population of particulates exhibits a median diameter (D50) of greater than 0.3 micrometer on a volume-average basis as determined using a Particle Size Test Method of the description, further wherein the radiation curable composition exhibits a viscosity of less than 150 Pa·s when measured using a Viscosity Test Method of the description; and
    (b) selectively exposing a portion of the radiation curable composition to a source of actinic radiation to at least partially cure the exposed portion of the radiation curable composition, thereby forming a hardened layer, wherein steps (a) and (b) are repeated to form a near net-shape composite article.

11. The method of claim 10, further comprising at least one of heating the radiation curable composition, removing uncured radiation curable composition from the near net-shape composite article, washing the near net-shape composite article with a solvent, or heating the near net-shape composite article.

12. A composite article prepared with the radiation curable composition of claim 1, wherein the composite article is a dental restoration.

13. The composite article of claim 12, wherein the dental restoration is selected from the group consisting of a crown, a bridge, an inlay, an onlay, a veneer, a pontic, or a combination thereof.

14. A system comprising:
    a display that displays a 3D model of a dental restoration; and
    one or more processors that, in response to the 3D model selected by a user, cause an additive manufacturing device to create a near net-shape composite dental restoration using an additive manufacturing method, the additive manufacturing method comprising the steps of:
    (a) providing a radiation curable composition, the radiation curable composition further comprising:
       at least one radiation hardenable component;
       an optical brightener in an amount of 0.01-1% by weight, based on the total weight of the radiation curable composition;
       a photo-initiator; and a filler material comprising a population of particulates in an amount greater than or equal to 50% by weight of the printable composition, wherein the population of particulates comprises a nano-filler, wherein the nano-filler comprises nano-clusters, and wherein the population of particulates exhibits a median diameter (D50) of greater than 0.3 micrometer on a volume-average basis as determined using a Particle Size Test Method of the description, further wherein the radiation curable composition exhibits a viscosity of less than 150 Pa·s when measured using a Viscosity Test Method of the description; and (b) selectively exposing a portion of the radiation curable composition to a source of actinic radiation to at least partially cure the exposed portion of the radiation curable composition, thereby forming a hardened layer, wherein steps (a) and (b) are repeated sequentially or continuously to form the near net-shape composite dental restoration.

15. The radiation curable composition of claim 1, wherein the nanoclusters have a specific surface area of from 30 to 400 $m^2/g$ and comprise particles selected from the group consisting of $SiO_2$, $ZrO_2$, $Al_2O_3$, and mixtures thereof.

16. The radiation curable composition of claim 1, wherein the nanoclusters are present in an amount from 5 to 40 weight percent based on the total weight of the radiation curable composition.

* * * * *